United States Patent
Weiss et al.

(10) Patent No.: US 10,966,977 B2
(45) Date of Patent: Apr. 6, 2021

(54) COMBINATION OF ANTI-CD20 ANTIBODY, P13 KINASE-DELTA SELECTIVE INHIBITOR, AND BTK INHIBITOR TO TREAT B-CELL PROLIFERATIVE DISORDERS

(71) Applicants: TG Therapeutics, Inc., New York, NY (US); Rhizen Pharmaceuticals SA, La Chaux de Fonds (CH); Laboratoire Francais Du Fractionnement Et Des Biotechnologies, Les Ulis (FR)

(72) Inventors: Michael S. Weiss, New York, NY (US); Hari P. Miskin, New York, NY (US); Peter Sportelli, New York, NY (US)

(73) Assignees: TG Therapeutics, Inc., New York, NY (US); Rhizen Pharmaceuticals SA, La Chaux de Fonds (CH); Laboratoire Francais du Fractionnement et das Biotechnologies, Les Ulis (FR)

( * ) Notice: Subject to any disclaimer, the term of this patent is extended or adjusted under 35 U.S.C. 154(b) by 0 days.

(21) Appl. No.: 16/304,590

(22) PCT Filed: May 26, 2017

(86) PCT No.: PCT/US2017/034855
§ 371 (c)(1),
(2) Date: Nov. 26, 2018

(87) PCT Pub. No.: WO2017/205843
PCT Pub. Date: Nov. 30, 2017

(65) Prior Publication Data
US 2019/0175592 A1   Jun. 13, 2019

Related U.S. Application Data

(60) Provisional application No. 62/342,822, filed on May 27, 2016.

(51) Int. Cl.
A61K 31/4985 (2006.01)
C07K 16/28 (2006.01)
(Continued)

(52) U.S. Cl.
CPC ........ *A61K 31/4985* (2013.01); *A61K 9/0019* (2013.01); *A61K 31/416* (2013.01);
(Continued)

(58) Field of Classification Search
CPC ............ A61K 2300/00; A61K 31/4985; A61K 31/506; A61K 31/519; A61K 39/3955;
(Continued)

(56) References Cited

U.S. PATENT DOCUMENTS 9,150,579 B2  10/2015  Vakkalanka
9,475,818 B2  10/2016  Vakkalanka
(Continued)

FOREIGN PATENT DOCUMENTS

WO   WO2011/055215 A2   5/2011
WO   WO2014/006572 A1   1/2014
(Continued)

OTHER PUBLICATIONS

Fowler et al. (Journal of clinical oncology, 33 (15), 2015, 8501-8501)).*
(Continued)

*Primary Examiner* — Savitha M Rao
(74) *Attorney, Agent, or Firm* — Wilson IP Law; M. Lisa Wilson

(57) ABSTRACT

Methods for inhibiting proliferation of a B-cell population are provided comprising administering a combination of agents, comprising: (i) at least one P13K-delta selective inhibitor; (ii) at least one anti-CD20 antibody; and (iii) at least one Bruton's tyrosine kinase (BTK) inhibitor. Methods for treating B-cell proliferative disorders, such as B-cell (Continued)

Figure 1:
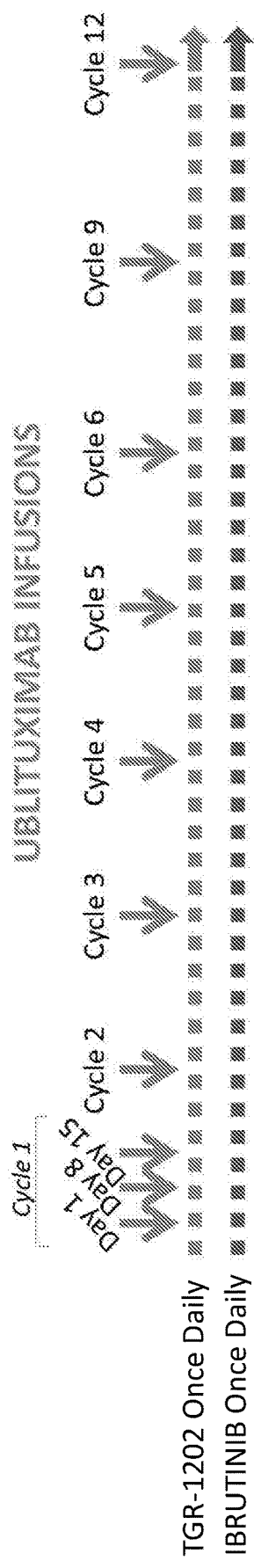

Study Design (TGR-1202 + Ublituximab + Ibrutinib)

Dose Escalation Schema:

| Cohort | Ublituximab Dose | TGR Dose (QD) | Ibrutinib (QD) |
|--------|------------------|---------------|----------------|
| 1 | 900 mg | 400 mg | 420 mg CLL / 560 mg NHL |
| 2 | 900 mg | 600 mg | 420 mg CLL / 560 mg NHL |
| 3 | 900 mg | 800 mg | 420 mg CLL / 560 mg NHL |

Treatment Schedule:

hematological malignancies, as well as kits for carrying out the claimed methods, are also provided.

20 Claims, 4 Drawing Sheets

Specification includes a Sequence Listing.

(51) Int. Cl.
    *A61K 31/506* (2006.01)
    *A61K 31/519* (2006.01)
    *A61K 45/06* (2006.01)
    *A61K 39/395* (2006.01)
    *A61P 35/02* (2006.01)
    *A61K 9/00* (2006.01)
    *A61K 31/4155* (2006.01)
    *A61K 31/416* (2006.01)

(52) U.S. Cl.
    CPC ........ *A61K 31/4155* (2013.01); *A61K 31/506* (2013.01); *A61K 31/519* (2013.01); *A61K 39/3955* (2013.01); *A61K 45/06* (2013.01); *A61P 35/02* (2018.01); *C07K 16/2887* (2013.01); *C07K 2317/24* (2013.01); *C07K 2317/41* (2013.01); *C07K 2317/732* (2013.01)

(58) Field of Classification Search
    CPC .. A61K 31/4155; A61K 31/416; A61K 45/06; A61K 9/0019; A61P 35/02; C07K 16/2887; C07K 2317/24; C07K 2317/41; C07K 2317/732
    See application file for complete search history.

(56) References Cited

U.S. PATENT DOCUMENTS

| | | | |
|---|---|---|---|
| 9,669,033 | B2 | 6/2017 | Vakkalanka |
| 9,694,071 | B2 | 7/2017 | Weiss |
| 10,072,013 | B2 | 9/2018 | Vakkalanka |
| 10,272,083 | B2 | 4/2019 | Hamdy |
| 2011/0118572 | A1 | 5/2011 | Muthuppalaniappan |
| 2014/0011819 | A1 | 1/2014 | Vakkalanka |
| 2015/0290317 | A1 | 10/2015 | Weiss |
| 2017/0121336 | A1 | 5/2017 | Vakkalanka |

FOREIGN PATENT DOCUMENTS

| | | |
|---|---|---|
| WO | WO2014/071125 A1 | 5/2014 |
| WO | WO2015/181728 A1 | 12/2015 |
| WO | WO2016/024232 A1 | 2/2016 |

OTHER PUBLICATIONS

Burris et al. (2014) J. Clin. Oncol. 32:2513. Activity of TGR-1202, a novel once-daily PI3Kδ inhibitor, in patients with relapsed or refractory hematologic malignancies.
Burris et al. (2016) J. Clin. Oncol. 34:7512. Long-term follow-up of the PI3Kδ inhibitor TGR-1201 to demonstrate a differentiated safety profile and high response rates in CLL and NHL: Integrated-anaysis of TGR-1202 monotherapy and combined with ublituximab; published May 20, 2016.
Davids et al. (2016) Blood 128:641. TGR-1202 in Combination with Ibrutinib in Patients with Relapsed or Refractory CLL or MCL: Preliminary Results of a Multicenter Phase I/IIb Study; Dec. 2, 2016.
Fowler et al. (2015) J. Clin. Oncol. 33:8501. Safety and activity of the chemotherapy-free triplet of ublituximab, TGR-1202 , and ibrutinib in relapsed B-cell malignancies; published May 20, 2015.
Kolibaba et al. (2015) Blood 126:3980. Ublituximab (TG-1101), A Novel Glycoengineered Anti-CD20 Monoclonal Antibody, in Combination with Ibrutinib is Highly Active in Patients with Relapsed and/or Refractory Mantle Cell Lymphoma: Results of a Phase II Trial; Dec. 3, 2015.
Lunning et al. (2015) Blood 126:1538. Ublituximab + TGR-1202 Demonstrates Activity and a Favorable Safety Profile in Relapsed/ Refractory B-Cell NHL and High-Risk CLL: Phase I Results; Dec. 3, 2015.
Nastoupil et al. (2015) Hematol. Oncol. 33:106. The Chemotherapy-Free Triplet of Ublituximab, TGR-1202, and Ibrutinib is Safe and Highly Active in Relapsed B-Cell Malignancies; Jun. 19, 2015.
Nastoupil et al. (2017) J. Clin. Oncol. 35:7511. Tolerability and activity of chemo-free triplet combination of TGR-1202, Ublituximab and ibrutinib in patients with advanced CLL and NHL; May 20, 2017.
Powers (2015) OncLive, Online Article. Ibrutinib, Ublituximab, TGR-1202 Triplet Active in Relapsed B-Cell Malignancies, reporting on 13th International Conference on Malignant Lymphoma, held Jun. 17-20, 2015 in Lugano, Switzerland; published Jun. 19, 2015.
Sharman et al. (2014) Blood 124:4679. Ublituximab (TG-1101), a Novel Glycoengineered Anti-CD20 Monoclonal Antibody, in Combination with Ibrutinib is Highly Active in Patients with Relapsed and/or Refractory CLL and MCL: Results of a Phase II Trial.
Sharman et al. (2015) Hematol. Oncol. 33:105. Ublituximab (TG-1101), a Novel Glycoengineered Anti-CD20 Monoclonal Antibody, in Combination with Ibrutinib Achieves 95% ORR in Patients with High-Risk Relapsed/Refracto CLL; Jun. 19, 2015.
Sharman et al. (2016) British J. Haematol. 176:412-420. Ublituximab (TG-1101), a Novel Glycoengineered Anti-CD20 Antibody, in Combination with Ibrutinib is Safe and Highly Active in Patients with Relapsed/Refractory Chronic lymphocytic leukemia: Results of a Phase II Trial; published Dec. 16, 2016.
Burris et al. (2018) Lancet Oncol. 19:486-496. Umbralisib, a novel PI3Kδ and casein kinase-1ε inhibitor, in relapsed or refractory chronic lymphocytic leukaemia and lymphoma: an open-label, phase 1, dose-escalation, first-in-human study; epub Feb. 20, 2018.
Bryd et al. (2014) N. Engl. J. Med. 371:213-223. Ibrutinib versus Ofatumumab in Previously Treated Chronic Lymphoid Leukemia.
Lunning et al. (2019) Blood 134:1811-1820. Ublituximab and umbralisib in relapsed/refractory B-cell non-Hodgkin lymphoma and chronic lymphocytic leukemia.
Nastoupil et al. (2019) Lancet Haematol. 6:e100-e109. Tolerability and activity of ublituximab, umbralisib, and ibrutinib in patients with chronic lymphocytic leukaemia and non-Hodgkin lymphoma: a phase 1 dose escalation and expansion trial.

* cited by examiner

Results
Efficacy

| Type | Pts (n) | CR† (n) | PR (n) | ORR n(%) | SD (n) | PD (n) |
|---|---|---|---|---|---|---|
| CLL/SLL | 19 | 6 | 13 | 19 (100%) | - | - |
| MZL | 2 | 1 | 1 | 2 (100%) | - | - |
| MCL | 4 | 2 | 2 | 4 (100%) | - | - |
| FL | 5 | 1 | 3 | 4 (80%) | 1 | - |
| DLBCL | 6 | - | 1 | 1 (17%) | - | 5 |
| Total | 36 | 10 | 20 | 30 (83%) | 1 | 5 |

†CLL: Radiographic CR's pending bone marrow confirmation

FIG. 4

COMBINATION OF ANTI-CD20 ANTIBODY, PI3 KINASE-DELTA SELECTIVE INHIBITOR, AND BTK INHIBITOR TO TREAT B-CELL PROLIFERATIVE DISORDERS

This application is a national stage filing under 35 U.S. § 371 of Intl. Appln. No. PCT/US2017/034855, filed May 26, 2017, which claims priority under 35 U.S.C. § 119(e) of provisional application U.S. Ser. No. 62/342,822, filed May 27, 2016.

BACKGROUND OF THE INVENTION

Field of the Invention

The present invention relates generally to the field of cancer therapy. More particularly, the present invention relates to methods and kits for inhibiting proliferation of a B-cell population and treating B-cell proliferative disorders, such as hematological cancers, by administering to a subject a combination of agents comprising: (i) at least one inhibitor of PI3 kinase (PI3K)-delta; (ii) at least one anti-CD20 antibody; and (iii) at least one inhibitor of Bruton's tyrosine kinase (BTK).

Background Art

Despite more than a century of dedicated scientific and clinical research, curing cancer remains one of the biggest medical challenges to date. Cancer treatments have mainly relied on the combination of surgery, radiotherapy, and/or cytotoxic chemotherapies. Within the last decade, however, targeted cancer therapies have opened a new era in the field of oncology. Targeted cancer therapies are drugs designed to interfere with specific molecules necessary for tumor growth and progression; they are broadly classified into monoclonal antibodies (mAbs) or small molecules. Some examples of targeted therapies include monoclonal antibodies to CD20 (e.g., rituximab/Rituxan® for treating lymphomas), CD52 (e.g., alemtuzumab/Campath®), VEGF (e.g., bevacizumab/Avastin®), HER2 (e.g., trastuzumab/Herceptin® for treating Her2+ breast and stomach cancers), EGFR (e.g., cetuximab/Erbitux® for treating colorectal cancer), CTLA-4 (e.g., ipilimumab/Yervoy® for treating melanoma), and PD-1 (e.g., MDX-1106, CT-011). Small molecule therapies target dysregulated pathways of cancer cells, e.g., RAS, RAF, PI3K, MEK, JAK, STAT, and BTK.

While effective B-cell cancer therapies exist (e.g., Rituxan®), suboptimal response and/or resistance to one or more therapeutic agents have remained a challenge. Accordingly, there is a need in the art for more effective, safe, and durable combination therapies for the treatment of B-cell proliferative diseases, such as B-cell malignancies.

BRIEF SUMMARY OF THE INVENTION

The combination treatment described herein is suitable for treating or delaying progression of B-cell proliferative disorders in a subject, such as hematological malignancies.

In one aspect, provided herein are methods of inhibiting proliferation of a B-cell population comprising (a) administering to the B-cell population a combination of agents, in therapeutically effective amounts, said combination of agents comprising: (i) at least one PI3K-delta selective inhibitor; (ii) at least one anti-CD20 antibody; and (iii) at least one inhibitor of Bruton's tyrosine kinase (BTK); and (b) inhibiting proliferation of said B-cell population.

In some embodiments, the PI3K-delta inhibitor is selected from the group consisting of TGR-1202 (also known as umbralisib), idelalisib, duvelisib (IPI-145), ACP-319; INCB-50465; and ME-401.

In another aspect, provided herein are methods of inhibiting proliferation of a B-cell population comprising,
(a) administering to said B-cell population a combination of agents, in therapeutically effective amounts, said combination of agents comprising:
(i) at least one PI3K delta selective inhibitor of Formula A, or a stereoisomer thereof, or a pharmaceutically acceptable salt, solvate, or prodrug thereof:

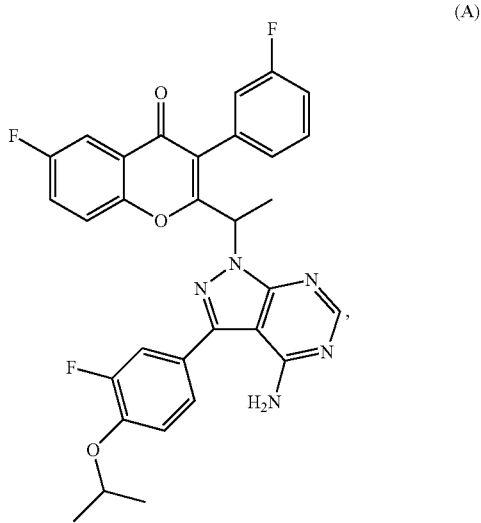 [SMILES: CC(C)Oc1ccc(-c2nn(C(C)c3oc4ccc(F)cc4c(=O)c3-c3cccc(F)c3)c3ncnc(N)c23)cc1F]

(A)

selected from one or more of,
(RS)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(ii) at least one anti-CD20 antibody, wherein at least one anti-CD20 antibody is ublituximab or an anti-CD20 antibody or antibody fragment that binds to the same epitope as ublituximab; and
(iii) at least one inhibitor of Bruton's tyrosine kinase (BTK); and
(b) inhibiting proliferation of said B-cell population.

In some embodiments, the PI3K-delta inhibitor of Formula A is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one.

In some embodiments, the PI3K-delta inhibitor of Formula A is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one p-toluenesulfonic acid (PTSA) salt (also known as TGR-1202).

In some embodiments, the method of inhibiting proliferation of a B-cell population comprises depleting B-cells. In some embodiments, such a method is used on a patient whose cancer has relapsed.

In some embodiments, the method of inhibiting proliferation of a B-cell population comprises promoting apoptosis of said B-cells.

In some embodiments, the method of inhibiting proliferation of a B-cell population comprises promoting cell-cycle arrest.

In some embodiments, the method of inhibiting proliferation of a B-cell population comprises blocking the B-cell receptor (BCR) signaling pathway.

In some embodiments, the P13K-delta inhibitor is administered daily at a dosage from: about 200 mg to about 1200 mg, about 400 mg to about 1000 mg, about 400 mg to about 800 mg, about 400 mg, about 500 mg, about 600 mg, about 700 mg, about 800 mg, about 900 mg, about 1000 mg, or about 1200 mg.

In some embodiments, TGR-1202 is administered at a dose of about 400 mg to about 1200 mg per day. In some embodiments, the TGR-1202 is administered at a dose of about 400 mg per day. In some embodiments, the TGR-1202 is administered at a dose of about 600 mg per day. In some embodiments, the TGR-1202 is administered at a dose of about 800 mg per day.

In some embodiments, the P13K-delta inhibitor is formulated for oral administration. In some embodiments, the P13K-delta inhibitor is TGR-1202 and it is formulated for oral administration. In some embodiments, TGR-1202 is administered in a fed-state.

In some embodiments, the anti-CD20 antibody is glyco-engineered, exhibits a low fucose content in its Fc region, or is antibody-dependent cellular cytotoxicity (ADCC)-optimized.

In some embodiments, the anti-CD20 antibody is ublituximab (also known as TG-1101 and UTX). In some embodiments, the ublituximab comprises the VH CDR1, CDR2, and CDR3 region of sequences SEQ ID NOS: 1, 2, and 3, and the VL CDR1, CDR2, and CDR3 region of sequences SEQ ID NOS: 6, 7, and 8. In some embodiments, the ublituximab comprises the VH of SEQ ID NO: 4 and the VL of SEQ ID NO: 9.

In some embodiments, the ublituximab is administered at a dose from: about 450 mg to about 1200 mg, about 600 to about 1200 mg, about 600 to about 1000 mg, about 600 to about 900 mg, about 600 mg, about 700 mg, about 800 mg, or about 900 mg.

Ublituximab may be administered about twice every week, about once every 1 to 9 weeks, about once every week, about once every 2 weeks, about once every 3 weeks, about once every 4 weeks, about once every 5 weeks, about once every 6 weeks, about once every 7 weeks, about once every 8 week, or about once every 9 weeks. One skilled in the art will appreciate that the dosage of ublituximab and/or frequency of administering ublituximab may change during the course of therapy (lowered or increased) depending upon the patient's clinical response, side effects, etc.

In some embodiments, the ublituximab is administered at a dose of about 900 mg. In some embodiments, the ublituximab is administered intravenously. Preferably, the ublituximab is administered by intravenous infusion.

In some embodiments, the BTK inhibitor is selected from the group consisting of 1-[(3R)-3-[4-Amino-3-(4-phenoxyphenyl)-1H-pyrazolo[3,4-d]pyrimidin-1-yl]piperidin-1-yl]prop-2-en-1-one (Imbruvica®, ibrutinib, or PCI-32765); 1-(R)-3-[4-amino-3-(4-phenoxyphenyl)-1H-pyrazolo[3,4-d]pyrimidin-1-yl]piperidin-1-yl]-2,3-dihydroxypropan-1-one (PCI-45227); 4-{8-Amino-3-[(2S)-1-(2-butynoyl)-2-pyrrolidinyl]imidazo[1,5-a]pyrazin-1-yl}-N-(2-pyridinyl)benzamide (acalabrutinib or ACP-196); (R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide (GDC-0834); (S)-9-(1-acryloylpiperidin-3-yl)-6-amino-7-(4-phenoxyphenyl)-7,9-dihydro-8H-purin-8-one (ONO-4059 or GS-4059); 6-cyclopropyl-8-fluoro-2-[2-(hydroxymethyl)-3-[1-methyl-5-[[5-(4-methylpiperazin-1-yl)pyridin-2-yl]amino]-6-oxopyridin-3-yl]phenyl]isoquinolin-1-one (RN-486); N-(3-((5-fluoro-2-((4-(2-methoxyethoxy)phenyl)amino)pyrimidin-4-yl)amino)phenyl)acrylamide (spebrutinib or AVL-292 or CC-292); SNS-062, as developed by Sunesis Pharmaceuticals and Biogen, see, Binnerts, M. E. et al., 2015 AACR-NCI-EORTC International Conference on Molecular Targets and Cancer Therapeutics, Boston, Mass., Nov. 8, 2015); N-(3-((2-((4-(4-methylpiperazin-1-yl)phenyl)amino)thieno[3,2-d]pyrimidin-4-yl)oxy)phenyl)acrylamide (HM-71224); 4-(tert-butyl)-N-(3-(8-(phenylamino)imidazo[1,2-a]pyrazin-6-yl)phenyl)benzamide (CGI-560); N-[3-[4,5-dihydro-4-methyl-6-[[4-(4-morpholinylcarbonyl)phenyl]amino]-5-oxopyrazinyl]-2-methylphenyl]-4-(1,1-dimethylethyl)-benzamide (CGI-1746); 4-(4-((4-((3-acrylamidophenyl)amino)-5-fluoropyrimidin-2-yl)amino)phenoxy)-N-methylpicolinamide (CNX-774); 7-benzyl-1-(3-(piperidin-1-yl)propyl)-2-(4-(pyridin-4-yl)phenyl)-1H-imidazo[4,5-g]quinoxalin-6(5H)-one (CTA-056); α-Cyano-β-hydroxy-β-methyl-N-(2,5-dibromophenyl)propenamide (LFM-A13); N-(2-chloro-6-methylphenyl)-2-[[6-[4-(2-hydroxyethyl)piperazin-1-yl]-2-methylpyrimidin-4-yl]amino]-1,3-thiazole-5-carboxamide (Sprycel® or Dasatinib or BMS-354825); BGB-3111, as developed by Beigene Co. Ltd., see, Tam, C. et al., Abstract #832, Am. Society Hematology (ASH) Annual Meeting, Orlando, Fla., Dec. 5-8, 2015); ONO-WG-307, as developed by Ono Pharmaceuticals, see, Kozaki, R. et al., *Cancer Res* 72(8 Suppl):Abstract No. 857 (2012); Yasuhiro, T. et al., *Cancer Res* 72(8 Suppl):Abstract No. 2021 (2012); JTE-051, as developed by Japan Tobacco Inc.; AVL-263 or CC-263, as developed by Avila Therapeutics/Celgene Corporation; AVL-291 or CC-291 and AVL-101 or CC-101, as developed by Avila Therapeutics/Celgene Corporation, see, Evans, E. et al., Paper presented at the 100th AACR Annual Meeting; Apr. 18-22, 2009; Denver, Colo.; see also D'Cruz, O. J. et al., *Onco Targets Ther.* 6: 161-176 (2013); TP-4207, as developed by Tolero Pharmaceuticals, Inc.; PCI-45292, as developed by Pharmacyclics, Inc., see, Chang, B. Y. et al., *Arthritis Rheum* 62:Suppl. 10, Abstract No. 286 (2010); Pan, Z. et al., Chem Med Chem 2:58-61 (2007); PCI-45466, as developed by Pharmacyclics, Inc., see, U.S. Patent Appl. Publ. 2016/0038495; CG-036806, as developed by Crystal Genomics; TAS-5567, as developed by Taiho Oncology, see, Kawagishi, A. et al., *Mol Cancer Ther* 12(11 Suppl)(2013): A274 and Irie, H. et al., *Mol Cancer Ther* 12(11 Suppl): A273 (2013); PCI-45261, as developed by Pharmacyclics, Inc.; KBP-7536, as developed by KBP BioSciences, see, e.g., U.S. Patent Appl. Publ. 2015/0267261; HCl-1684, as developed by Huntsman Cancer Institute, see, Bearss, D. J. et al., *Cancer Res* 71(8 Suppl):Abstract No. 2788 (2011); PLS-123, as developed by Peking University Cancer Hospital, see, Ding, N. et al., *Oncotarget* 6: 15122-15136 (April 2015); BMS-488516, as developed by Bristol-Myers Squibb, see, Lin, T. A. et al., *Biochemistry* 43:11056-11062 (2004); Won, J. et al., *International Reviews of Immunology* 27:19-41 (2008); BMS-509744, as developed by Bristol-Myers Squibb, see, Lin, T. A. et al., *Biochemistry* 43:11056-11062 (2004); Won, J. et al., *International Reviews of Immunology* 27:19-41 (2008); Benzamide, N-[5-[[5-[(4-acetyl-1-piperazinyl)carbonyl]-4-methoxy-2-methylphenyl]

thio]-2-thiazolyl]-4-[[(1,2-dimethylpropyl)amino]methyl]- (HY-11066, CTK417891, HMS3265G21, HMS3265G22, HMS3265H21, HMS3265H22, CAS No. 439574-61-5, AG-F-54930).

In some embodiments, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one (ibrutinib).

In some embodiments, the BTK inhibitor is 4-{8-Amino-3-[(2S)-1-(2-butynoyl)-2-pyrrolidinyl]imidazo[1,5-a]pyrazin-1-yl}-N-(2-pyridinyl)benzamide (acalabrutinib or ACP-196).

In some embodiments, the ibrutinib is administered once daily at a dosage from: about 200 to about 800 mg, about 400 to about 600 mg, about 400 mg, about 420 mg, about 440 mg, about 480 mg, about 500 mg, about 520 mg, about 540 mg, about 560 mg, about 580 mg, or about 600 mg.

In some embodiments, the ibrutinib is administered once daily at a dosage of about 420 mg or about 560 mg per day. In some embodiments, the ibrutinib is administered once daily at a dosage of about 420 mg per day. In some embodiments, the ibrutinib is administered once daily at a dosage of about 560 mg per day.

In some embodiments, ibrutinib is administered orally.

In some embodiments, the B-cell population whose proliferation is to be inhibited is in a human subject. In some embodiments, the human subject has a disease or disorder associated with excessive B-cell proliferation. In some embodiments, the disease associated with excessive B-cell proliferation is cancer. In some embodiments, a human subject has cancer. In some embodiments, the cancer is a B-cell hematological malignancy. In certain embodiments, the B-cell hematological malignancy is lymphoma or leukemia.

In some embodiments, the B-cell hematological malignancy is selected from the group consisting of acute lymphocytic leukemia (ALL), acute myeloid leukemia (AML), acute monocytic leukemia (AMoL), chronic lymphocytic leukemia (CLL), high-risk CLL, small lymphocytic lymphoma (SLL), high-risk SLL, multiple myeloma (MM), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), Burkitt's lymphoma (BL), hairy cell leukemia (HCL), and Richter's transformation.

In some embodiments, the B-cell hematological malignancy is selected from the group consisting of chronic lymphocytic leukemia (CLL), small lymphocytic lymphoma (SLL), non-Hodgkin's lymphoma (NHL), mantle cell lymphoma (MCL), follicular lymphoma (FL), diffuse large B-cell lymphoma (DLBCL), and marginal zone lymphoma (MZL).

In some embodiments, the hematological malignancy is selected from the group consisting of Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, plasma cell myeloma, plasmacytoma, mediastinal (thymic) large B cell lymphoma, intravascular large B cell lymphoma, primary effusion lymphoma, Hodgkin's lymphoma, or lymphomatoid granulomatosis.

In some embodiments, the cancer overexpresses CD20.

In some embodiments, the cancer is refractory to chemotherapy.

In some embodiments, the cancer is refractory to any agent described herein, i.e., an anti-CD20 antibody, a P13K delta selective inhibitor, or a BTK inhibitor, when said agent was administered individually (i.e., used as a monotherapy).

In some embodiments, the cancer is refractory to non-TGR-1202 P13K-delta inhibitors.

In some embodiments, the cancer is refractory to non-ublituximab anti-CD20 antibodies.

In some embodiments, the cancer is refractory to rituximab.

In some embodiments, the cancer is refractory to a BTK inhibitor.

In some embodiments, the cancer is refractory to ibrutinib.

In some embodiments, the cancer has relapsed.

In some embodiments, the human subject has one or more genetic mutations selected from the group consisting of 17p del, 11q del, p53, unmutated IgVH together with ZAP-70+ and/or CD38+, and trisomy 12.

In some embodiments, the agents (i, ii, and iii) of the methods described herein are administered separately.

In some embodiments, the agents (i, ii, and iii) of the methods described herein are administered sequentially, though a particular order (or sequence of administration) is not required. In some embodiments, the agents (i and iii) of the methods described herein are administered simultaneously or sequentially.

In some embodiments, the combination of agents is sequentially administered in an induction, consolidation, and/or maintenance regimen.

In some embodiments, two of the agents i, ii, or iii, are administered together in order to induce a partial anti-tumor response, followed by administration of the third agent to enhance the anti-tumor response. In some embodiments, a complete anti-tumor response (CR) is observed following administration of all agents (e.g., i, ii, and iii, as disclosed herein) to said subject. In some embodiments, a subject administered any of the methods described herein achieves a complete response with minimal residual disease (MRD).

In some embodiments, a subject administered any of the methods described herein achieves a partial reponse (PR) when all three agents are administered in combination. In some embodiments, a subject administered any of the methods described herein achieves a partial response (PR) or a complete response (CR) that is durable for at least two months.

In some embodiments, at least one of the agents i, ii, or iii, is administered in a maintenance therapy in order to keep the B-cell proliferative disorder from returning after successful treatment. In some embodiments, the agent is administered in maintenance therapy for an extended period of time, e.g., until unmanageable toxicity, or disease progression occurs. In some embodiments, the maintenance therapy ends when disease progression occurs.

In some embodiments, the agents (i and iii) of the methods described herein are contained in the same pharmaceutical composition. In some embodiments, the pharmaceutical composition is for oral administration.

In some embodiments, the methods described herein further comprises administering to the subject at least one additional therapeutic agent for inhibiting B-cell proliferation. In some embodiments, the at least one additional therapeutic agent is selected from the group consisting of mitotic inhibitors, alkylating agents, anti-metabolites, anthracyclines, *vinca* alkaloids, plant alkaloids, nitrogen mustards, proteasome inhibitors, intercalating antibiotics, growth factor inhibitors, cell-cycle inhibitors, biological response modifiers, anti-hormones, angiogenesis inhibitors, anti-androgens, DNA interactive agents, purine analogues, topoisomerase I inhibitors, topoisomerase II inhibitors, tubulin interacting agents, hormonal agents, thymidilate synthase inhibitors, non-BTK and non-P13K-delta tyrosine kinase inhibitors, angiogenesis inhibitors, EGF inhibitors, VEGF inhibitors, CDK inhibitors, SRC inhibitors, c-Kit inhibitors, Her1/2 inhibitors, inhibitors of myc, anti-tumor antibodies, monoclonal antibodies directed against growth factor receptors, protein kinase modulators, radioactive isotopes, immunotherapies, glucocorticoids, and combinations thereof.

In some embodiments, the at least one additional therapeutic agent is an anti-cancer agent selected from the group consisting of DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate; other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); and other protein kinase modulators. Other anti-cancer agents that could be used in the methods and kits of the invention will be known to those skilled in the oncology art.

In some embodiments, the at least one additional therapeutic agent is selected from the group consisting of a proteasome inhibitor, Bortezomib (Velcade®), Carfilzomib (PR-171), PR-047, disulfiram, lactacystin, PS-519, eponemycin, epoxomycin, aclacinomycin, CEP-1612, MG-132, CVT-63417, PS-341, vinyl sulfone tripeptide inhibitors, ritonavir, PI-083, (+/−)-7-methylomuralide, (−)-7-methylomuralide, lenalidomide, and combinations thereof.

In some embodiments, the additional therapeutic agent is a combination of chemotherapies such as, e.g., "CHOP" (a combination including (i) cyclophosphamide such as cytoxan, (ii) doxorubicin or other topoisomerase II inhibitors such as adriamycin, (iii) vincristine or other vincas such as oncovin; and (iv) a steroid such as hydrocortisone or prednisolone); "R-CHOP" (a combination including rituxan, cyclophosphamide, doxorubicin, vincristine, and prednisone); "ICE" (a combination including ifosfamide, carboplatin, and etoposide); "R-ICE" (a combination including rituxan, ifosfamide, carboplatin, and etoposide); "R-ACVBP" (a combination of rituximab, doxorubicin, cyclophosphamide, vindesine, bleomycin and prednisone); "DA-EPOCH-R" (a combination of dose-adjusted etoposide, doxorubicin, cyclophosphamide, vincristine, prednisone and rituximab); "R-bendamustine" (a combination of bendamustine and rituximab); "GemOx or R-GemOx" (a combination of gemcitabine and oxaliplatin, with or without rituximab); and "DHAP" (a combination including dexamethasone, cytarabine, and cisplatin).

In some embodiments, methods of inhibiting proliferation of a B-cell population are provided, comprising, (a) administering to the B-cell population a combination of agents, in therapeutically effective amounts, said combination of agents comprising: (i) TGR-1202; (ii) ublituximab; and (iii) ibrutinib; and (b) inhibiting proliferation of said B-cell population.

In some embodiments, the proliferation of the B-cell population is associated with a hematological malignancy. In some embodiments, the hematological malignancy is selected from the group consisting of acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), Burkitt's lymphoma, hairy cell leukemia (HCL), and Richter's transformation.

In one aspect, provided herein is a kit comprising at least one P13K-delta selective inhibitor, at least one anti-CD20 antibody, and at least one inhibitor of BTK; and (b) instruction for using a P13K-delta selective inhibitor in combination with an anti-CD20 antibody and an inhibitor of BTK.

In another aspect, provided herein is a kit comprising at least one P13K-delta selective inhibitor of formula A, at least one anti-CD20 antibody, and at least one inhibitor of BTK. In certain embodiments, other agents that can be used to perform the methods described herein, and combinations thereof, are also included in the kit.

In some embodiments, the kit comprises (a) a P13K-delta selective inhibitor of formula A, as described herein, or a stereoisomer thereof, or a pharmaceutically acceptable salt, solvate, or prodrug thereof; an anti-CD20 antibody or fragment thereof that binds to the same epitope as ublituximab; and an inhibitor of BTK; and (b) instructions for using said P13K-delta selective inhibitor, in combination with ublituximab or an anti-CD20 antibody or fragment thereof that binds to the same epitope as ublituximab and an inhibitor of BTK.

In some embodiments, the inhibitor of BTK in the kit is ibrutinib. In some embodiments, the inhibitor of BTK in the kit is acalabrutinib.

In some embodiments, the P13K-delta selective inhibitor in the kit is (S)-2-(1-(4-amino-3-(3-fluoro-4-isopropoxyphenyl)-H-pyrazolo[3,4-d]pyrimidin-1-yl)ethyl)-6-fluoro-3-(3-fluorophenyl)-4H-chromen-4-one. In some embodiments, the P13K-delta selective inhibitor in the kit is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one p-toluenesulfonic acid (PTSA) salt (TGR-1202).

In some embodiments, the kit further comprises ublituximab or an anti-CD20 antibody or fragment thereof that binds to the same epitope as ublituximab.

In some embodiments, the kit further comprises one or more additional therapeutic agents that can be used to inhibit B-cell proliferation.

BRIEF DESCRIPTION OF THE DRAWINGS/FIGURES

FIG. 1 is a schematic representation of the study design of a Phase 1/1b clinical trial where TGR1202+ Ublituximab+ Ibrutinib were administered to 38 patients with NHL (n=22) and CLL (n=16). Patients with NHL included those with DLBCL, FL, MCL, SLL, and MZL. Details of patient histologies are provided in Example 1. TGR-1202 and Ibrutinib were administered once daily starting on day 1. Ublituximab infusions were given on day 1, 8, and 15 of cycle 1, and day 1 of cycles 2, 3, 4, 5, 6, 9, and 12 (as indicated by the arrow (↓)).

Figure 2:
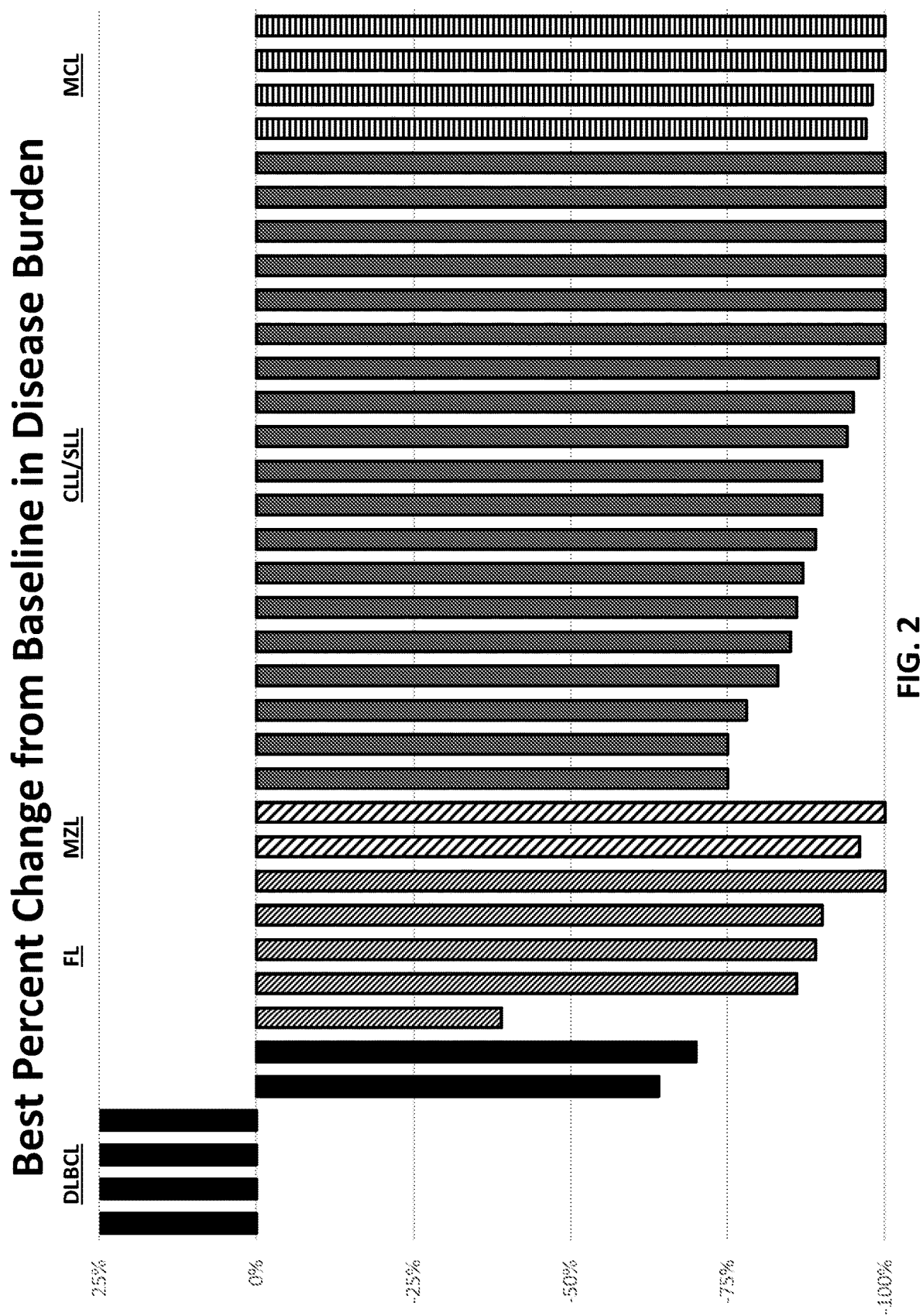

FIG. 2 is a bar graph depicting efficacy of the combination of TGR-1202+ Ublituximab+Ibrutinib in 36 patients with CLL and NHL. Efficacy is reflected in the best percent change from baseline in disease burden in all patients who had received at least one post baseline scan to assess disease/tumor burden, with responses determined according to standard international working group criteria for NHL and CLL (see citations in Example 1).

Figure 3:
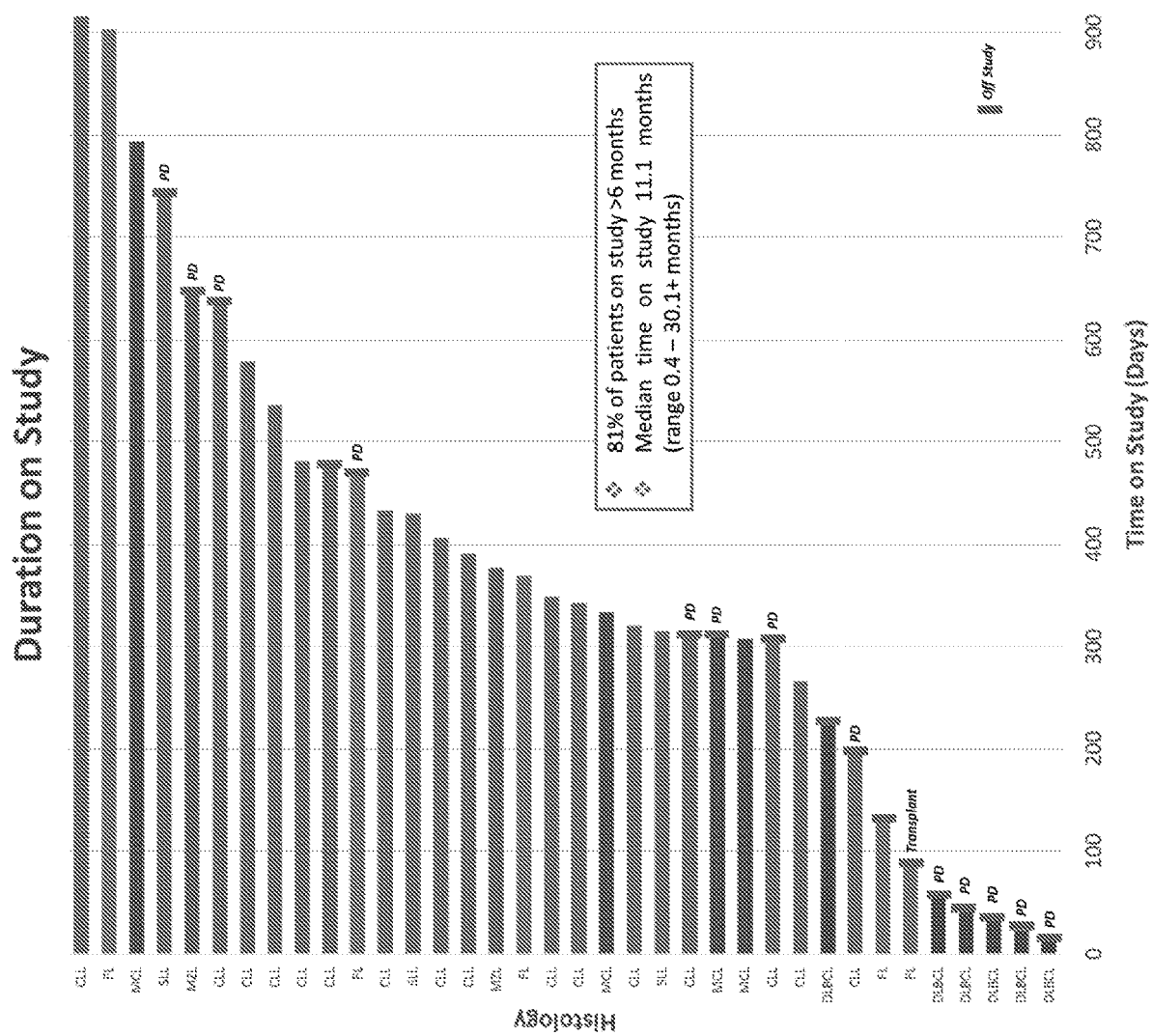

FIG. 3 is a bar graph depicting the number of days (duration) that patients with various histologies were on the study. Eighty one percent of patients were on study for more than six months. The median time on the study was 11.1 months (range 0.4-30.1+ months). "PD" indicates progressive disease.

FIG. 4 is a Table depicting efficacy of the combination of TGR-1202+ Ublituximab+Ibrutinib in 36 patients with CLL and NHL, as reflected in the rate of clinical response (i.e., complete response (CR); partial response (PR); overall response rate (ORR); stable disease (SD); progressive disease (PD).

DETAILED DESCRIPTION OF THE INVENTION

Definitions

To facilitate an understanding of the present invention, a number of terms and phrases are defined below.

The term "CD20" (also known as B lymphocyte CD20 antigen, MS4A1, B lymphocyte surface antigen B1, Bp35, and Leukocyte surface antigen Leu-16) refers to any native CD20, unless otherwise indicated. As used herein, the term "CD20" encompasses "full-length," unprocessed CD20, as well as any form of CD20 that results from processing within the cell. The term also encompasses naturally occurring variants of CD20, e.g., splice variants, allelic variants, and isoforms. The CD20 polypeptides described herein can be isolated from a variety of sources, such as from human tissue types or from another source, or prepared by recombinant or synthetic methods. Examples of CD20 sequences include, but are not limited to, NCBI reference numbers NP_068769.2 and NP_690605.1.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as CD20. In a certain embodiment, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-CD20 antibody" or "an antibody that binds to CD20" refers to an antibody that is capable of binding CD20 with sufficient affinity such that the antibody is useful as a diagnostic and/or therapeutic agent in targeting CD20. The extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of ≤1 µM, ≤100 nM, ≤10 nM, ≤1 nM, or ≤0.1 nM.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies, as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., *Nature* 321:522-525 (1986); Riechmann et al., *Nature* 332:323-327 (1988); Verhoeyen et al., *Science* 239:1534-1536 (1988)). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs), also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al, *J. Molec. Biol.* 273: 927-948 (1997)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest. 5$^{th}$ Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5$^{th}$ Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop, when numbered using the Kabat numbering convention, varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
|  |  | (Kabat Numbering) | |
| H1 | H31-H35 | H26-H35 | H26-H32 |
|  |  | (Chothia Numbering) | |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability, while the constant regions are homologous to the sequences in antibodies derived from another (usually human) to avoid eliciting an immune response in that species.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described herein.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better," the antibody's affinity for the antigen is <0.6 nM, i.e., 0.59 nM, 0.58 nM, 0.57 nM etc. or any value less than 0.6 nM.

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristics measured by said values (e.g., Kd values). The difference between said two values is less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The terms "cancer" and "cancerous" refer to or describe the physiological condition in mammals in which a population of cells are characterized by uncontrolled or unregulated cell growth. Examples of cancer include, e.g., carcinoma, lymphoma, blastoma, sarcoma, and leukemia.

As used herein, the term "B-cell proliferative disorder" or "B-cell lymphoproliferative disorder" refers to a disease or disorder in a subject wherein a population of B-cells in the subject are produced in excessive quantities, such as seen in B-cell malignancies (B-cell cancers).

The term "B-cell cancer" or "B-cell malignancy" refers to an uncontrolled or unregulated growth of B-cells in the blood, bone marrow, or lymph node. One skilled in the art would understand that a B-cell malignancy is a type of hematological malignancy that includes lymphomas, leukemias, and myelomas. The B-cell malignancy may be indolent or aggressive. Non-limiting examples of hematological malignancies that may be treated with the methods or kits of the invention include acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), which includes extranodal MZL, nodal MZL, and splenic MZL, hairy cell leukemia (HCL), Burkitt's lymphoma (BL), and Richter's transformation. In some embodiments, the DLBCL is an activated B-cell DLBCL (ABC-DLBCL), a germinal center B-cell like DLBCL (GBC-DLBCL), a double hit DLBCL (DH-DLBCL), or a triple hit DLBCL (TH-DLBCL). In some embodiments, certain CLLs (or other leukemias, such as the ones described herein) are considered "high risk" due to the presence of one of more genetic mutations. As used herein, "high risk" CLL, for example, means CLL characterized by at least one of the following genetic mutations: 17p del; 11q del; p53; unmutated IgVH together with ZAP-70+ and/or CD38+; and trisomy 12.

"Tumor" and "neoplasm" refer to any mass of tissue that result from excessive cell growth or proliferation, either benign (noncancerous) or malignant (cancerous) including pre-cancerous lesions.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

A cell "population" can refer to a single cell or to multiple cells. The cell or cells can be cells in culture (in vitro) or cells in an organism (in vivo). For example, a cell population can be in a human subject or patient. A "B-cell population" refers to a single B-cell or multiple B-cells. One skilled in the art would understand that a "B-cell" (also known as a "B lymphocyte") refers to a type of white blood cell (WBC) of the lymphocyte subtype. B cells function in the humoral immunity component of the adaptive immune system by secreting antibodies.

The term "pharmaceutical formulation" refers to a preparation which is in such form as to permit the biological activity of the active ingredient to be effective, and which contains no additional components which are unacceptably toxic to a subject to which the formulation would be administered. Such formulations can be sterile.

An "effective amount" of an antibody or an agent as disclosed herein, is an amount sufficient to carry out a specifically stated purpose. An "effective amount" can be determined empirically and in a routine manner by those skilled in the art, in relation to the stated purpose.

The term "therapeutically effective amount" refers to the amount of an agent (e.g., monoclonal antibody, small molecule, chemotherapeutic drug, etc. . . . ), as disclosed herein, that is effective to "treat" a disease or disorder in a subject or mammal. In the case of cancer, the therapeutically effective amount of the agent or drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; and/or relieve to some extent one or more of the symptoms associated with the cancer. See the definition herein of "treating." To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

Terms such as "treating," "treatment," "to treat," "having a therapeutic effect," alleviating," "to alleviate," or "slowing the progression of" refer to both 1) therapeutic measures that cure, slow down, lessen symptoms of, and/or halt progression of a diagnosed pathologic condition or disorder, such as a hematological malignancy, and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: reduction in cachexia, increase in survival time, elongation in time to tumor progression, reduction in tumor mass, reduction in tumor burden and/or a prolongation in time to tumor metastasis, time to tumor recurrence or progressive disease, tumor response, complete response (CR), partial response (PR), stable disease, progression free survival (PFS), overall survival (OS), each as measured by standards set by the National Cancer Institute and the U.S. Food and Drug Administration for the approval of new drugs. See, Johnson et al, *J. Clin. Oncol.* 21:1404-1411 (2003). In some embodiments, the "therapeutic effect," as defined above, also encompasses a reduction in toxicity or adverse side effects, and/or an improvement in tolerability.

A "combination" of an anti-CD20 antibody (e.g., ublituximab), a P13K-delta selective inhibitor (e.g., TGR-1202), and a BTK inhibitor (e.g., ibrutinib), is generally synonymous with a "combination of agents." A "combination of agents" refers to the administration of at least one of each of these three agents (could be more than one type of each agent) to the same population of B-cells or to the same subject simultaneously, sequentially, or both simultaneously and sequentially. Thus, by way of example, administration of an anti-CD20 antibody preceding or following (e.g., by hour(s), day(s), week(s), or month(s)) administration of a P13K-delta selective inhibitor, preceding or following (e.g., by hour(s), day(s), week(s), or month(s)) administration of a BTK inhibitor, constitutes administration of a combination of agents. As will be apparent to one skilled in the art from the context, a "combination of agents" can also include an anti-CD20 antibody (e.g., ublituximab), a P13K-delta selective inhibitor (e.g., TGR-1202), and a BTK inhibitor, and one or more additional therapeutic agents, as described herein. In addition, simultaneous administration of an anti-CD20 antibody or fragment thereof, a P13K-delta selective inhibitor, and a BTK inhibitor also constitutes administration of a combination of the anti-CD20 antibody or fragment thereof, P13K-delta selective inhibitor, and a BTK inhibitor, regardless of whether the anti-CD20 antibody or fragment thereof, P13K-delta inhibitor, and the BTK inhibitor are administered together in a single pharmaceutical formulation or are administered simultaneously in separate pharmaceutical formulations by either the same or different routes of administration. Further, the term "combination of agents" is intended to include treatment regimens in which the agents are administered by the same or different route of administration or at the same or different time.

As used herein, the term "induction" or "induction therapy" refers to the first agent, or combination of agents, as disclosed herein, administered to treat a B-cell proliferative disorder. If the first agent or combination of agents does not result in a complete response or it causes severe side effects, other agents may be added or used instead (see "consolidation"). Induction is also called primary therapy, or primary treatment, and is administered with the goal of inducing some initial reduction in disease burden. For example, induction therapy can include the use of an anti-CD20 inhibitor and a P13K delta inhibitor.

As used herein, "consolidation" or "consolidation therapy" refers to treatment that is given following induction therapy. Consolidation therapy is used to kill any malignant B-cells that may be left in the body following induction therapy. For example, if an anti-CD20 inhibitor and a P13K delta inhibitor are used as induction therapy, consolidation therapy can include the use of a BTK inhibitor. Consolidation is also called intensification therapy.

As used herein, "maintenance" or "maintenance therapy" refers to treatment that is given to help keep the B-cell proliferative disorder from returning after successful treatment with the initial therapy. Maintenance therapy may include treatment with the same agents that were used in the consolidation phase, and the agents in this phase may be administered for an extended period of time.

A tumor which "does not respond," "responds poorly," or is "refractory" to treatment (with, for example, an anti-CD20 antibody) does not show statistically significant improvement in response to that treatment when compared to no treatment or treatment with a placebo in a recognized animal model or human clinical trial, or which responds to an initial treatment, but grows as treatment continues.

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST can be used as described in Altschul et al., *Nucleic Acids Res.*, 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* 48:444-453 (1970)), can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value therebetween, or over a longer region than 60-80 residues, at least about 90-100 residues, or the sequences are substantially identical over the full length of the sequences being compared, such as the coding region of a nucleotide sequence for example.

All numbers in this disclosure indicating amounts, ratios of materials, physical properties of materials, and/or use are to be understood as modified by the word "about," except as otherwise explicitly indicated. The term "about" when referring to a number or a numerical range means that the number or numerical range referred to is an approximation within experimental variability (or within statistical experimental error), and thus the number or numerical range can vary from, for example, between 1% and 15% of the stated number or numerical range.

The compound of the invention can contain one or more asymmetric centers (chiral centers) and can thus give rise to enantiomers, diastereomers, and other stereoisomeric forms that can be defined, in terms of absolute stereochemistry, as (R)- or (S)-. The present disclosure is meant to encompass all such possible forms, as well as their racemic and resolved forms and mixtures thereof. The individual enantiomers can be separated according to methods known in the art in view of the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation, concentration or depletion of one of the two enantiomeric forms of a molecule.

The present disclosure encompasses solvates of compounds of the invention. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the invention can be present as solvated forms with a pharmaceutically acceptable solvent, such as water, methanol, ethanol, and the like, and it is intended that the disclosure includes both solvated and unsolvated forms of compounds of the invention. One type of solvate is a hydrate. A "hydrate" relates to a particular subgroup of solvates where the solvent molecule is water. Solvates typically can function as pharmacological equivalents. Preparation of solvates is known in the art. See, e.g., Caira, M. et al., *J. Pharmaceut. Sci.* 93:601-611 (2004); van Tonder, E. C. et al., *AAPSPharm. Sci. Tech.* 5(1):Article 12 (2004); and Bingham, A. L. et al., *Chem. Commun.* 603-604 (2001). A typical, non-limiting, process of preparing a solvate would involve dissolving a compound of the invention in a desired solvent (organic, water, or a mixture thereof) at temperatures about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The term "prodrug" refers to a compound, which is an inactive precursor of a compound, converted into its active form in the body by normal metabolic processes. Prodrug design is discussed generally in Hardman, J. G. et al. (eds.), *Goodman and Gilman's The Pharmacological Basis of Therapeutics*, 9$^{th}$ ed., pp. 11-16 (1996). A thorough discussion is provided in Higuchi et al., *Prodrugs as Novel Delivery Systems*, Vol. 14, ASCD Symposium Series, and in Roche (ed.), *Bioreversible Carriers in Drug Design*, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound. Prodrugs of the compounds of the invention are intended to be covered within the scope of this invention.

The present invention also includes compounds which differ only in the presence of one or more isotopically enriched atoms, for example, replacement of hydrogen with deuterium or tritium, or the replacement of a carbon by $^{13}$C- or $^{14}$C-enriched carbon. The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The present disclosure further encompasses salts of the compounds of the invention, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate, succinates, palmoates, benzoates, salicylates, ascorbates, glycerophosphates, ketoglutarates and the like; sulfonates such as methanesulfonate, benzenesulfonate, p-toluenesulfonate and the like; salts of natural amino acids such as glycine, alanine, valine, leucine, isoleucine, norleucine, tyrosine, cystine, cysteine, methionine, proline, hydroxy proline, histidine, omithine, lysine, arginine, and serine; and salts of non-natural amino acids such as D-isomers or substituted amino acids; salts of guanidine; and salts of substituted guanidine wherein the substituents are selected from nitro, amino, alkyl, alkenyl, alkynyl, ammonium or substituted ammonium salts and aluminum salts.

The term "selective inhibitor" as applied to a biologically active agent refers to the agent's ability to selectively reduce the target signaling activity as compared to off-target signaling activity, via direct or indirect interaction with the target.

The term "P13K-delta selective inhibitor" (also known as P13K-δ inhibitor) refers to a compound, which selectively inhibits the activity of the P13K-delta isoform more effectively than other isoforms of the P13K family (α, β, and γ). In some embodiments, the P13K-delta selective inhibitor refers to a compound of Formula A, as described herein, which selectively inhibits the activity of the P13K-delta isoform more effectively than other isoforms of the P13K family (α, β, and γ). For instance, a P13K-delta selective inhibitor of Formula A can be a compound that exhibits a 50% inhibitory concentration ($IC_{50}$) with respect to the δ type P13-kinase that is at least 20-fold, or lower, than the inhibitor's $IC_{50}$ with respect to the rest of the other types P13K isoforms (i.e., α, β, and γ).

The term "Bruton's tyrosine kinase" (also known as "BTK," agammaglobulinemia tyrosine kinase (ATK), or B-cell progenitor kinase (BPK)) refers to a non-receptor tyrosine kinase enzyme in the B-cell antigen receptor (BCR) signaling pathway. BTK, a member of the Tec family of protein tyrosine kinases, is predominantly expressed in B-lymphocytes at various stages of development (except in terminally differentiated plasma cells). BTK is a signal transduction protein that regulates normal B-cell development, differentiation and functioning, and has also been implicated in initiation, survival, and progression of mature B-cell lymphoproliferative disorders, such as B-cell malignancies. Akinleye, A. et al., *J. Hematol. Oncol.* 6:59 (2013). As used herein, BTK is from *Homo sapiens*, as disclosed in U.S. Pat. No. 6,326,469 (Gen Bank Acc. No. NP_000052).

An "inhibitor of BTK" or "BTK inhibitor" refers to a small molecule that targets BTK and either inhibits BTK tyrosine phosphorylation and/or B-cell activation and/or otherwise inhibits or diminishes or abolishes the biological activity of a BTK protein. An "irreversible BTK inhibitor" refers to a molecule that upon contact with BTK, causes the formation of a new covalent bond with an amino acid residue of BTK. Both reversible and irreversible inhibitors of BTK can be used in the methods and kits of the present invention.

The term "synergistic effect," as used herein, refers to a greater-than-additive therapeutic effect produced by a combination administration of compounds wherein the therapeutic effect obtained with the combination exceeds the additive effects that would otherwise result from individual administration the compounds alone. Embodiments of the invention include methods of producing a synergistic effect in the treatment of hematological cancer, wherein said effect is at least 5%, at least 10%, at least 20%, at least 30%, at least 40%, at least 50%, at least 60%, at least 70%, at least 80%, at least 90%, at least 100%, at least 200%, at least 500%, or at least 1000% greater than the corresponding additive effect.

"Therapeutic synergy," as used herein, means that the combined administration of agents, as described herein, (i.e., an anti-CD20 antibody and a P13K-delta selective inhibitor of Formula A and a BTK inhibitor) produces a therapeutic effect that is greater than the additive effects of the anti-CD20 antibody, the P13K-delta selective inhibitor, and the BTK inhibitor, when each is used alone and/or when two agents are combined.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

Methods

In one aspect, provided herein are methods of inhibiting proliferation of a B-cell population comprising (a) administering to the B-cell population a combination of agents, in therapeutically effective amounts, said combination of agents comprising: (i) at least one P13K-delta selective inhibitor; (ii) at least one anti-CD20 antibody; and (iii) at least one inhibitor of Bruton's tyrosine kinase (BTK); and (b) inhibiting proliferation of said B-cell population.

In another aspect, provided herein are methods of inhibiting proliferation of a B-cell population comprising, (a) administering to said B-cell population a combination of agents, in therapeutically effective amounts, said combination of agents comprising:

(i) at least one P13K-delta selective inhibitor of Formula A, or a stereoisomer thereof, or a pharmaceutically acceptable salt, solvate, or prodrug thereof:

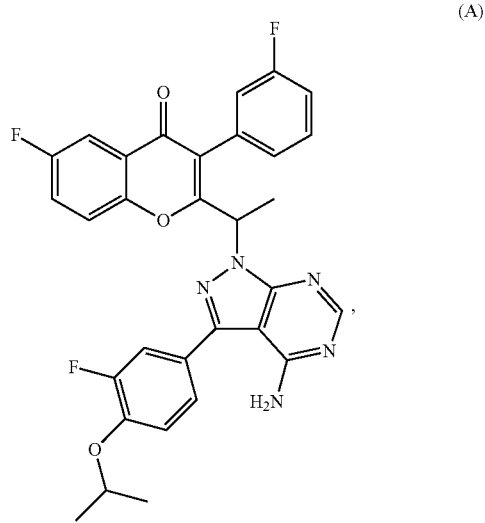 [SMILES: CC(C)Oc1ccc(-c2nn(C(C)c3oc4ccc(F)cc4c(=O)c3-c3cccc(F)c3)c3ncnc(N)c23)cc1F]

(A)

selected from one or more of, (RS)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;

(ii) at least one anti-CD20 antibody, wherein at least one anti-CD20 antibody is ublituximab or an anti-CD20 antibody or antibody fragment that binds to the same epitope as ublituximab; and (iii) at least one inhibitor of Bruton's tyrosine kinase (BTK); and (b) inhibiting proliferation of said B-cell population.

In some embodiments, the method of inhibiting proliferation of a B-cell population comprises depleting B-cells. In some embodiments, this method is effective on subjects whose cancer has relapsed.

In some embodiments, the method of inhibiting proliferation of a B-cell population comprises promoting apoptosis of said B-cells.

In some embodiments, the method of inhibiting proliferation of a B-cell population comprises promoting cell-cycle arrest.

In some embodiments, the method of inhibiting proliferation of a B-cell population comprises depleting B-cells.

In some embodiments, the method of inhibiting proliferation of a B-cell population comprises blocking the B-cell receptor (BCR) signaling pathway.

In some embodiments, the method of inhibiting proliferation of a B-cell population treats a B-cell proliferative disorder in a subject. In some embodiments, the B-cell proliferative disorder is a hematological malignancy. In some embodiments, the hematological malignancy is selected from the group consisting of acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), Burkitt's lymphoma (BL), hairy cell leukemia (HCL), and Richter's transformation.

P13K-Delta Selective Inhibitor

The phosphoinositide 3-kinases (P13Ks) are a family of enzymes that regulate diverse biological functions in every cell type by generating phosphoinositide second-messenger molecules. P13Ks are involved in various cellular functions, including cell proliferation and survival, cell differentiation, intracellular trafficking, and immunity. As the activity of these phosphoinositide second messengers is determined by their phosphorylation state, the kinases and phosphatises that act to modify these lipids are central to the correct execution of intracellular signaling events. P13Ks phosphorylate lipids at the 3-hydroxyl residue of an inositol ring (Whitman et al., Nature 332:664 (1988)) to generate phosphorylated phospholipids (PIP3s), which act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase PTEN (Phosphatase and Tensin homolog deleted on chromosome Ten) dephosphorylates PIP3 and therefore acts as a negative regulator of Akt activation. The P13Ks Akt and PDK1 are important in the regulation of many cellular processes including cell cycle regulation, proliferation, survival, apoptosis, and motility and are significant components of the molecular mechanisms of diseases such as cancer, diabetes, and immune inflammation (Vivanco et al., Nature Rev. Cancer 2:489 (2002); Phillips et al., Cancer 83:41 (1998)).

The P13K family is comprised of four different classes: Classes I, II, III, and IV. Classes I-III are lipid kinases and Class IV are serine/threonine protein kinases.

The members of the Class I family of P13Ks are dimers of a regulatory and a catalytic subunit. The Class I family consists of four isoforms, determined by the 110 kDa catalytic subunits α, β, γ, and δ. See Engelman, J. A., *Nat Rev Genet* 7:606-619 (2006); Carnero, A., *Curr Cancer Drug Targets* 8:187-198 (2008); and Vanhaesebroeck, B., *Trends Biochem Sci* 30:194-204 (2005). Class I can be subdivided into two subclasses: Class Ia, formed by the combination of p110 α, β, and δ, and a regulatory subunit (p85, p55 or p50); and Class Ib, formed by p110 γ and p101 regulatory subunits. The delta (δ) isoform of P13K is highly expressed in cells of hematopoietic origin, and strongly upregulated, and often mutated, in various hematologic malignancies.

Studies regarding P13K and related protein kinase pathways have been published by various groups, including, Liu et al., *Nature Reviews Drug Discovery* 8:627-644 (2009); Nathan et al, *Mol. Cancer Ther.* 8(1) (2009); and Marone et al., *Biochimica et Biophysica Acta* 1784:159-185 (2008). Two known inhibitors of P13K, LY294002 and Wortmannin, are non-specific P13K inhibitors as they do not distinguish the four members of Class I P13K: α, β, γ, and δ. A number of P13K inhibitors have entered clinical trials for the treatment of cancers, and various types of cancers (including breast cancer, non-small cell lung cancer (NSCLC), and hematological cancers), are being considered as areas of therapeutic interest.

One example of a P13K-delta selective inhibitor is Idelalisib (trade name Zydelig®), which was approved by the U.S. FDA in 2014 for the treatment of relapsed CLL (in combination with Rituxan®; see, Furman, R. R. et al., *N. Eng. J. Med.* 370:997-1007 (2014)), relapsed follicular B-cell non-Hodgkin lymphoma (FL), and relapsed small lymphocytic lymphoma (SLL) another type of non-Hodgkin lymphoma. See, Zydelig® full prescribing information (Gilead Sciences). Idelalisib has a unique and limiting toxicity profile including immune mediated colitis (grade 3≥5%), pneumonitis (grade 3≥4%), and transaminitis (grade 3≥8%). Therefore the FDA's approval of Zydelig® comes with a boxed warning noting the possibility of fatal and serious toxicities including hepatic, severe diarrhea, colitis, pneumonitis and intestinal perforation. Id.

Another example of a P13K-delta selective inhibitor is duvelisib (IPI-145). See, O'Brian, S. et al., *Blood* 124: Abstract 3334 (2014). Although duvelisib targets both P13K delta and gamma, at the dose under development (25 mg twice daily), it primarily inhibits just the delta isoform. Id. Another P13K-delta selective inhibitor is ACP-319 (previously AMG-319). See, Lanasa, M. C. et al., *Blood* 122: Abstract 678 (2013). ACP-319 is currently in development by Acerta Pharma B.V, ME-401 is a new oral P13K-delta selective inhibitor in development by MEI Pharma. See, Moreno, O. et al., "Clinical Pharmacokinetics and Pharmacodynamics of ME-401, an Oral, Potent, and Selective Inhibitor of Phosphatidylinositol 3-Kinase P110δ, Following Single Ascending Administration to Healthy Volunteers" (Abstract # CT157), presented at the American Association for Cancer Research (AACR) Annual Meeting, New Orleans (April 16-20, 2016). INCB-50465 is another P13K-delta selective inhibitor in development by Incyte Corporation that is in Phase I/II clinical trials for the treatment of B-cell malignancies. See, Forero-Torres, A. et al., "Preliminary safety, efficacy, and pharmacodynamics of a highly selective PI3Kδ inhibitor, INCB050465, in patients with previously treated B-cell malignancies" (Abstract #CT056), presented at the AACR Annual Meeting, New Orleans (Apr. 16-20, 2016).

As provided herein, at least one P13K-delta selective inhibitor is used in the methods (and kits) of the present invention. In one embodiment, the P13K-delta selective inhibitor that is used in combination with the anti-CD20 antibodies and BTK inhibitors, described herein, is a compound of formula A:

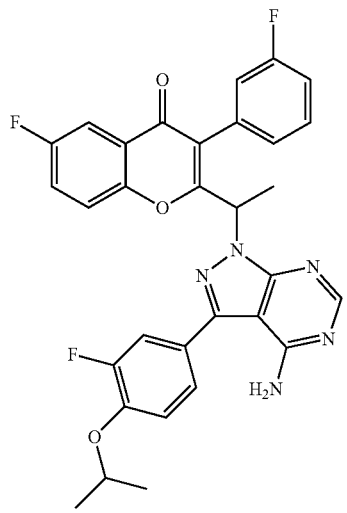

(A)

or a stereoisomer thereof, or a pharmaceutically acceptable salt, solvate, or prodrug thereof. In a preferred embodiment, the compound of Formula A is selected from one or more of, (RS)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one.

A P13K-delta inhibitor of formula A can be prepared using the general synthetic methods as disclosed in International Patent Appl. Publ. No. WO 2011/055215 A2 and U.S. Patent Appl. Publ. No. 2011/0118257 A1.

In some embodiments, the P13K-delta inhibitor is administered to a subject daily at a dosage from: about 200 mg to about 1200 mg, about 400 mg to about 1000 mg, about 400 mg to about 800 mg, about 400 mg, about 500 mg, about 600 mg, about 700 mg, about 800 mg, about 900 mg, about 1000 mg, or about 1200 mg.

In some embodiments, the P13K-delta inhibitor of Formula A is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one.

In a preferred embodiment, the P13K-delta inhibitor of Formula A is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one p-toluenesulfonic acid (PTSA) salt (also known as (S)-2-(1-(4-amino-3-(3-fluoro-4-isopropoxyphenyl)-1H-pyrazolo[3, 4-d]pyrimidin-1-yl)-ethyl)-6-fluoro-3-(3-fluorophenyl)-4H-chromen-4-one 4-methylbenzenesulfonate, TGR-1202, and umbralisib).

The preparation of TGR-1202 is described in International Publ. No. WO 2014/006572 and U.S. Patent Publ. No. 2014/0011819, each of which is incorporated herein by reference in its entirety. In addition to describing the synthesis of TGR-1202, WO 2014/006572 and US 2014/0011819 also disclose the therapeutic activity of this molecule to inhibit, regulate and/or modulate the signal transduction of P13K. TGR-1202 is also described in U.S. Pat. No. 9,150,579, which issued Oct. 6, 2015. International Publ. No. WO 2015/181728, incorporated herein by reference in its entirety, describes a solid state form of TGR-1202 that exhibits enhanced solubility and pharmacokinetics upon oral administration. The entirety of each of these applications and patents is incorporated herein by reference.

TGR-1202 (or umbralisib) is a next generation P13K-delta inhibitor with a unique molecular structure and activity profile distinct from other P13K-delta inhibitors in development, including: (1) greater selectivity to the delta isoform of P13K; (2) a a prolonged half-life that enables once-daily dosing; and (3) a differentiated safety profile from other P13K-delta inhibitors, notably with respect to hepatic toxicity and colitis.

TGR-1202 was evaluated in a single-agent Phase I dose-escalation study in patients with relapsed and refractory hematologic malignancies (see e.g., Burris et al., "Activity of TGR-1202, a novel once-daily PI3Kδ inhibitor, in patients with relapsed or refractory hematologic malignancies," *J. Clinical Oncology* (ASCO Annual Meeting Abstracts) 32 (15): 2513 (2014)). The study reported that TGR-1202 was well-tolerated in patients with relapsed or refractory hematologic malignancies, with no reported hepatic toxicity and signs of clinical activity at doses≥800 mg each day. Id. The favorable safety profile of TGR-1202 compared to prior inhibitors has also been demonstrated in long-term follow up. See, Burris, H. et al., "Long-term follow-up of the P13K delta inhibitor TGR-1202 demonstrates a differentiated safety profile and high response rates in CLL and NI-IL: Integrated-analysis of TGR-1202 monotherapy and combined with ublituximab," American Society of Clinical Oncology Annual Meeting (ASCO). Abstract #7512 (Jun. 3, 2016).

In some embodiments, the TGR-1202 is administered at a dose from about 400 mg to about 1200 mg per day. In some embodiments, the TGR-1202 is administered at a dose of about 400 mg per day. In some embodiments, the TGR-1202 is administered at a dose of about 600 mg per day. In some embodiments, the TGR-1202 is administered at a dose of about 800 mg per day.

In some embodiments, the P13K-delta inhibitor is formulated for oral administration. In certain embodiments, the P13K-delta inhibitor is TGR-1202 and it is formulated for daily oral administration. In certain embodiments, TGR-1202 is administered in a fed-state.

Anti-CD20 Antibodies

CD20 is a hydrophobic transmembrane phosphoprotein that is expressed predominantly in pre-B cells and mature peripheral B cells in humans and mice. In humans, CD20 is also strongly and homogeneously expressed in most mature B-cell malignancies, including, for example, most non-Hodgkin's B-cell lymphomas (NHL) and B-type Chronic Lymphocytic Leukemia's (B-CLL). The CD20 antigen is not expressed on haematopoietic stem cells or on plasmocytes.

Anti-CD20 monoclonal antibodies have been, and continue to be, developed for the treatment of B-cell diseases. The chimeric anti-CD20 monoclonal antibody rituximab (Rituxan®) has become the standard therapy for many CD20-positive B-cell lymphomas and was the first mAb approved for any oncology indication. Demarest, S J et al., mAbs 3:338-351 (2011). However, there are a substantial number of patients who are refractory to treatment with rituximab or who develop resistance in the course of prolonged treatment with rituximab (used as a single agent or even in combination with chemotherapeutic regimens).

As provided herein, anti-CD20 antibodies and antigen-binding fragments thereof can be used in combination with a P13K-delta selective inhibitor and a BTK inhibitor to treat B-cell proliferative disorders, such as B-cell malignancies. More than one anti-CD20 antibody can be used in the methods and kits of the present invention.

Aside from rituximab, a number of other anti-CD20 antibodies are known in the art, including, for example, ublituximab, ofatumumab (HuMax; Intracel), ocrelizumab, veltuzumab, GA101 (obinutuzumab), AME-133v (Applied Molecular Evolution), ocaratuzumab (Mentrik Biotech), PRO131921, tositumomab, ibritumomab-tiuxetan, hA20 (Immunomedics, Inc.), BLX-301 (Biolex Therapeutics), Reditux (Dr. Reddy's Laboratories), and PRO70769 (described in WO2004/056312).

Rituximab is a genetically engineered chimeric murine/human monoclonal antibody directed against the CD20 antigen. Rituximab is the antibody called "C2B8" in U.S. Pat. No. 5,736,137. The amino acid sequence of rituximab antibody and exemplary methods for its production via recombinant expression in Chinese Hamster Ovary (CHO) cells are disclosed in U.S. Pat. No. 5,736,137, which is herein incorporated by reference in its entirety. Rituximab is commercially available as Rituxan®.

Ofatumumab is an anti-CD20 IgG1κ human monoclonal antibody. Studies indicate that ofatumumab dissociates from CD20 at a slower rate compared to the rituximab and binds a membrane-proximal epitope. Zhang et al., *Mabs* 1: 326-331 (2009). Epitope mapping has indicated that ofatumumab binds an epitope located closer to the N-terminus of CD20 compared to the location targeted by rituximab and includes an extracellular loop of the antigen. Id.

Ublituximab (also known as UTX, TG-1101, TGTX-1101, Utuxin™, LFB-R603, TG20, EMAB603) is a chimeric monoclonal antibody targeting a unique epitope on the CD20 antigen and that has been glycoengineered for enhanced affinity for all variants of Fcγ RIIIa receptors, thereby demonstrating greater antibody-dependent cellular cytotoxicity ("ADCC") activity than rituximab and ofatumab. See, Miller, J. et al., *Blood* 120: Abstract No. 2756 (2012); Deng, C. et. al., *J. Clin. Oncol.* 31:Abstract No. 8575 (2013); O'Connor, O. A. et al., *J. Clin. Oncol.* 33:5s (2014L (suppl; Abstract No. 8524). Ublituximab is also described in U.S. Pat. No. 9,234,045. Ublituximab was engineered for potent activity, exhibiting a unique primary amino acid sequence and allowing a low fucose content, designed to induce superior ADCC. Responses with single agent ublituximab were observed in rituximab refractory patients. Id.

In a preferred embodiment, the anti-CD20 antibody used in the methods (and kits) described herein is ublituximab (also known as TG-1101) or an anti-CD20 antibody that binds to the same epitope as ublituximab. In a particularly preferred embodiment, the anti-CD20 antibody is ublituximab. In some embodiments, the ublituximab comprises the VH CDR1, CDR2, and CDR3 region of sequences SEQ ID NOS: 1, 2, and 3, and the VL CDR1, CDR2, and CDR3 region of sequences SEQ ID NOS: 6, 7, and 8. In some embodiments, the ublituximab comprises the VH of SEQ ID NO: 4 and the VL of SEQ ID NO: 9.

Ublituximab comprises the antibody sequences provided below:

```
Variable heavy chain (VH) CDR1:
                                                                       (SEQ ID NO: 1)
Gly Tyr Thr Phe Thr Ser Tyr Asn Variable heavy chain (VH) CDR2:
                                                                       (SEQ ID NO: 2)
Ile Tyr Pro Gly Asn Gly Asp Thr Variable heavy chain (VH) CDR3:
                                                                       (SEQ ID NO: 3)
Ala Arg Tyr Asp Tyr Asn Tyr Ala Met Asp Tyr Variable heavy chain (VH):
                                                                       (SEQ ID NO: 4)
Gln Ala Tyr Leu Gln Gln Ser Gly Ala Glu Leu Val Arg Pro Gly Ala Ser Val Lys Met Ser
Cys Lys Ala Ser Gly Tyr Thr Phe Thr Ser Tyr Asn Met His Trp Val Lys Gln Thr Pro Arg
Gln Gly Leu Glu Trp Ile Gly Gly Ile Tyr Pro Gly Asn Gly Asp Thr Ser Tyr Asn Gln Lys
Phe Lys Gly Lys Ala Thr Leu Thr Val Gly Lys Ser Ser Ser Thr Ala Tyr Met Gln Leu Ser
Ser Leu Thr Ser Glu Asp Ser Ala Val Tyr Phe Cys Ala Arg Tyr Asp Tyr Asn Tyr Ala Met
Asp Tyr Trp Gly Gln Gly Thr Ser Val Thr Val Ser Ser Constant heavy chain:
                                                                       (SEQ ID NO: 5)
Ala Ser Thr Lys Gly Pro Ser Val Phe Pro Leu Ala Pro Ser Ser Lys Ser Thr Ser Gly Gly
Thr Ala Ala Leu Gly Cys Leu Val Lys Asp Tyr Phe Pro Glu Pro Val Thr Val Ser Trp Asn
Ser Gly Ala Leu Thr Ser Gly Val His Thr Phe Pro Ala Val Leu Gln Ser Ser Gly Leu Tyr
Ser Leu Ser Ser Val Val Thr Val Pro Ser Ser Ser Leu Gly Thr Gln Thr Tyr Ile Cys Asn
Val Asn His Lys Pro Ser Asn Thr Lys Val Asp Lys Lys Val Glu Pro Lys Ser Cys Asp Lys
Thr His Thr Cys Pro Pro Cys Pro Ala Pro Glu Leu Leu Gly Gly Pro Ser Val Phe Leu Phe
Pro Pro Lys Pro Lys Asp Thr Leu Met Ile Ser Arg Thr Pro Glu Val Thr Cys Val Val Val
Asp Val Ser His Glu Asp Pro Glu Val Lys Phe Asn Trp Tyr Val Asp Gly Val Glu Val His
Asn Ala Lys Thr Lys Pro Arg Glu Glu Gln Tyr Asn Ser Thr Tyr Arg Val Val Ser Val Leu
Thr Val Leu His Gln Asp Trp Leu Asn Gly Lys Glu Tyr Lys Cys Lys Val Ser Asn Lys
Ala Leu Pro Ala Pro Ile Glu Lys Thr Ile Ser Lys Ala Lys Gly Gln Pro Arg Glu Pro Gln
Val Tyr Thr Leu Pro Pro Ser Arg Asp Glu Leu Thr Lys Asn Gln Val Ser Leu Thr Cys
Leu Val Lys Gly Phe Tyr Pro Ser Asp Ile Ala Val Glu Trp Glu Ser Asn Gly Gln Pro Glu
Asn Asn Tyr Lys Thr Thr Pro Pro Val Leu Asp Ser Asp Gly Ser Phe Phe Leu Tyr Ser Lys
Leu Thr Val Asp Lys Ser Arg Trp Gln Gln Gly Asn Val Phe Ser Cys Ser Val Met His Glu
Ala Leu His Asn His Tyr Thr Gln Lys Ser Leu Ser Leu Ser Pro Gly Lys Variable light chain (VL) CDR1:
                                                                       (SEQ ID NO: 6)
Ser Ser Val Ser Tyr Variable light chain (VL) CDR2:
                                                                       (SEQ ID NO: 7)
Ala Thr Ser Variable light chain (VL) CDR3:
                                                                       (SEQ ID NO: 8)
Gln Gln Trp Thr Phe Asn Pro Pro Thr Variable light chain (VL):
                                                                       (SEQ ID NO: 9)
Gln Ile Val Leu Ser Gln Ser Pro Ala Ile Leu Ser Ala Ser Pro Gly Glu Lys Val Thr Met
Thr Cys Arg Ala Ser Ser Ser Val Ser Tyr Met His Trp Tyr Gln Gln Lys Pro Gly Ser Ser
```

-continued

```
Pro Lys Pro Trp Ile Tyr Ala Thr Ser Asn Leu Ala Ser Gly Val Pro Ala Arg Phe Ser Gly

Ser Gly Ser Gly Thr Ser Tyr Ser Phe Thr Ile Ser Arg Val Glu Ala Glu Asp Ala Ala Thr

Tyr Tyr Cys Gln Gln Trp Thr Phe Asn Pro Pro Thr Phe Gly Gly Gly Thr Arg Leu Glu Ile

Lys

Constant light chain:
                                                              (SEQ ID NO: 10)
Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys
```

In some embodiments, ublituximab is administered at a dose from: about 450 mg to about 1200 mg, about 600 to about 1200 mg, about 600 to about 1000 mg, about 600 to about 900 mg, about 600 mg, about 700 mg, about 800 mg, or about 900 mg. In certain embodiments, the ublituximab is administered at a dose of about 900 mg.

Ublituximab may be administered about once every 1 to 9 weeks, about once every week, about twice every week, about once every 2 weeks, about once every 3 weeks, about once every 4 weeks, about once every 5 weeks, about once every 6 weeks, about once every 7 weeks, about once every 8 week, or about once every 9 weeks. One skilled in the art will appreciate that the dosage of ublituximab and/or frequency of administering ublituximab may change during the course of therapy (lowered or increased) depending upon the patient's clinical response, side effects, etc. . . . .

In some embodiments, the ublituximab is administered intravenously, preferably by infusion.

In some embodiments, the anti-CD20 antibody or fragment thereof binds to the same epitope as ublituximab. In some embodiments, the anti-CD20 antibody or fragment thereof binds to a sequence comprising amino acids N153-S179 of CD20. In some embodiments, the anti-CD20 antibody or fragment thereof binds to a discontinuous epitope in amino acids N153-S179 of CD20.

In some embodiments, the anti-CD20 antibody or fragment thereof binds to CD20 with an affinity characterized by a dissociation constant KD of less than about $10^{-7}$ M, less than about $10^{-8}$ M or less than about $10^{-9}$ M. In some embodiments, the anti-CD20 antibody or fragment thereof binds to CD20 with an affinity characterized by a dissociation constant KD of $10^{-10}$ to $10^{-9}$ M. In some embodiments the anti-CD20 antibody or fragment thereof binds to CD20 with an affinity characterized by a dissociation constant KD of $0.7 \times 10^{-9}$ M. As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about 10-2 M" might include, for example, from 0.05 M to 0.005 M.

In some embodiments, the anti-CD20 antibody exhibits a high affinity to Fc-gammaRIII (CD16). In some embodiments, as a result of their high affinity for the Fc region of the antibody to CD16, such antibodies are not displaced by IgG polyclonal antibodies, especially by IgG present in blood serum. In some embodiments the antibody binds to CD16 (e.g., expressed on a macrophage) with an affinity of at least $2 \times 10^6$ $M^{-1}$, at least $2 \times 10^7$ $M^{-1}$, $2 \times 10^8$ $M^{-1}$ or $2 \times 10^7$ $M^{-1}$, e.g., as determined by Scatchard analysis or BIAcore technology (Label-free surface plasmon resonance based technology).

In some embodiments, the anti-CD20 antibody is glycoengineered. As used herein, a "glycoengineered" anti-CD20 antibody means that the sugar molecules (N-glycan) in the Fc region of the antibody have been altered or engineered, either genetically, enzymatically, chemically, or selected for during the manufacturing process. in order to, e.g., increase the affinity of the antibody for Fc receptors on effector cells and/or to reduce its specific carbohydrate content in its Fc region.

In some embodiments, the anti-CD20 antibody exhibits a glycosylation pattern characterized by low fucose content in its Fc region. For example, in some embodiments, a composition comprises anti-CD20 antibodies in which the antibodies comprise N-glycoside-linked sugar chains bound on the Fc-gamma glycosylation site (Asn 297, EU numbering), wherein among the N-glycoside-linked sugar chains of all the antibodies of the composition, the fucose content is less than 65%, less than 60%, less than 55%, less than 50%, less than 45%, or less than 40%. In some embodiments, among the N-glycoside-linked sugar chains of all the antibodies of the composition, the fucose content is 15 to 45% or 20 to 40%.

In some embodiments, the anti-CD20 antibody exhibits potent in vitro antibody-dependent cellular cytotoxicity (ADCC) and can be said to be "ADCC-optimized". In some embodiments, the anti-CD20 antibody produces an ADCC plateau of at least about 10%, at least about 15%, at least about 20%, at least about 25%, or at least about 30% at a concentration of 50 ng/ml using natural killer (NK) cells from healthy donors. Techniques for measuring ADCC are known in the art and provided, for example, in de Romeuf, C. et al., *British Journal of Haematology* 140: 635-643 (2008). In some embodiments, the anti-CD20 antibody produces an ADCC plateau at about 35% at a concentration of 50 ng/ml using NK cells from healthy donors.

In some embodiments, the anti-CD20 antibody can decrease NF-kappa-B activity. In some embodiments, the anti-CD20 antibody can decrease SNAIL expression. In some embodiments, the anti-CD20 antibody can increase RKIP activity. In some embodiments, the anti-CD20 antibody can increase PTEN activity. In some embodiments, the anti-CD20 antibody can increase sensitization of a cell to TRAIL-apoptosis.

In some embodiments, the anti-CD20 antibody is Fc-gamma-RIIIA (CD16) optimized. Antibodies capable of activating type III Fc receptors and having a particular glycan structure have been described, for example, in U.S. Pat. No. 7,931,895, which is herein incorporated by reference in its entirety. Thus, in some embodiments, the anti-CD20 antibody is modified on Asn 297 (EU numbering) with N-glycosylations of the bi-antennary and/or oligomannoside type as described in U.S. Pat. No. 7,931,895. Methods of producing antibodies with strong affinity for receptor CD16 of the effector cells of the immune system are provided, for example, in U.S. Published Appl. No. 2005/0271652, which is herein incorporated by reference in its entirety.

In some embodiments, the anti-CD20 antibody has high ADCC activity. Methods of producing antibodies with high ADCC activity are provided, for example, in U.S. Pat. No. 7,713,524, which is herein incorporated by reference in its entirety.

Thus, in some embodiments, an isolated antibody or antigen-binding fragment, variant, or derivative thereof comprises, consists essentially of, or consists of an immunoglobulin heavy chain variable domain (VH domain), wherein at least one (i.e., one, two, or three) of the CDRs of the VH domain has an amino acid sequence that is at least 80%, 85%, 90%, 95%, 96%, 97%, 98%, 99%, or identical to the CDR1, CDR2, or CDR3 region of sequences SEQ ID NO: 1, 2, or 3, wherein an antibody or antigen-binding fragment thereof comprising the VH domain can specifically or preferentially bind to CD20.

In another embodiment, an isolated antibody or antigen-binding fragment, variant, or derivative thereof comprises, consists essentially of, or consists of an immunoglobulin heavy chain variable domain (VH domain), wherein at least one (i.e., one, two, or three) of the CDRs of the VH domain has an amino acid sequence identical, except for 1, 2, 3, 4, or 5 conservative amino acid substitutions, to the CDR1, CDR2 or CDR3 region of sequences SEQ ID NO:1, 2, or 3, wherein an antibody or antigen-binding fragment, variant, or derivative thereof comprising the VH domain can specifically or preferentially bind to CD20.

In another embodiment, an isolated antibody or antigen-binding fragment, variant, or derivative thereof comprises, consists essentially of, or consists of a VH domain that has an amino acid sequence that is at least 80%, 85%, 90%, 91%, 92%, 93%, 94%, 95%, 96%, 97%, 98%, 99%, or 100% identical to a VH amino acid sequence of SEQ ID NO:4, wherein an antibody or antigen-binding fragment, variant, or derivative thereof comprising the VH domain can specifically or preferentially bind to CD20.

In another embodiment, an isolated antibody or antigen-binding fragment, variant, or derivative thereof comprises, consists essentially of, or consists of a heavy chain that has an amino acid sequence that is at least 80%, 85%, 90%, 91%, 92%, 93%, 94%, 95%, 96%, 97%, 98%, 99%, or 100% identical to a heavy chain amino acid sequence comprising SEQ ID NOs: 4 and 5, wherein an antibody or antigen-binding fragment, variant, or derivative thereof comprising the heavy chain can specifically or preferentially bind to CD20.

In some embodiments, an isolated antibody or antigen-binding fragment, variant, or derivative thereof comprises, consists essentially of, or consists of an immunoglobulin light chain variable domain (VL domain), wherein at least one (i.e., one, two, or three) of the CDRs of the VL domain has an amino acid sequence that is at least 80%, 85%, 90%, 95%, 96%, 97%, 98%, 99%, or identical to the CDR1, CDR2, or CDR3 region of sequences SEQ ID NO:6, 7, or 8, wherein an antibody or antigen-binding fragment thereof comprising the VL domain can specifically or preferentially bind to CD20.

In another embodiment, an isolated antibody or antigen-binding fragment, variant, or derivative thereof comprises, consists essentially of, or consists of an immunoglobulin light chain variable domain (VL domain), wherein at least one (i.e., one, two, or three) of the CDRs of the VL domain has an amino acid sequence identical, except for 1, 2, 3, 4, or 5 conservative amino acid substitutions, to the CDR1, CDR2, or CDR3 region of SEQ ID NO:6, 7, or 8, wherein an antibody or antigen-binding fragment, variant, or derivative thereof comprising the VL domain can specifically or preferentially bind to CD20.

In another embodiment, an isolated antibody or antigen-binding fragment, variant, or derivative thereof comprises, consists essentially of, or consists of a VL domain that has an amino acid sequence that is at least 80%, 85%, 90%, 91%, 92%, 93%, 94%, 95%, 96%, 97%, 98%, 99%, or 100% identical to a VL amino acid sequence of SEQ ID NO:9, wherein an antibody or antigen-binding fragment, variant, or derivative thereof comprising the VL domain can specifically or preferentially bind to CD20.

In another embodiment, an isolated antibody or antigen-binding fragment, variant, or derivative thereof comprises, consists essentially of, or consists of a light chain that has an amino acid sequence that is at least 80%, 85%, 90%, 91%, 92%, 93%, 94%, 95%, 96%, 97%, 98%, 99%, or 100% identical to a light chain amino acid sequence comprising SEQ ID NOs:9 and 10, wherein an antibody or antigen-binding fragment, variant, or derivative thereof comprising the light chain can specifically or preferentially bind to CD20.

In some embodiments, an isolated antibody or antigen-binding fragment, variant, or derivative thereof comprises, consists essentially of, or consists of an immunoglobulin heavy chain variable domain (VH domain) and an immunoglobulin light chain variable domain (VL domain), wherein at least one (i.e., one, two, or three) of the CDRs of the VH domain has an amino acid sequence that is at least 80%, 85%, 90%, 95%, 96%, 97%, 98%, 99%, or identical to the CDR1, CDR2, or CDR3 region of sequences SEQ ID NO:1, 2, or 3, wherein at least one (i.e., one, two, or three) of the CDRs of the VL domain has an amino acid sequence that is at least 80%, 85%, 90%, 95%, 96%, 97%, 98%, 99%, or identical to the CDR1, CDR2 or CDR3 region of sequences SEQ ID NO:6, 7, or 8, and wherein an antibody or antigen-binding fragment thereof comprising the VH domain and VL domain can specifically or preferentially bind to CD20.

In another embodiment, an isolated antibody or antigen-binding fragment, variant, or derivative thereof comprises, consists essentially of, or consists of an immunoglobulin heavy chain variable domain (VH domain), and an immunoglobulin light chain variable domain (VL domain), wherein at least one (i.e., one, two, or three) of the CDRs of the VH domain has an amino acid sequence identical, except for 1, 2, 3, 4, or 5 conservative amino acid substitutions, to the CDR1, CDR2, or CDR3 region of sequences SEQ ID NO: 1, 2, or 3, wherein at least one (i.e., one, two, or three) of the CDRs of the VL domain has an amino acid sequence identical, except for 1, 2, 3, 4, or 5 conservative amino acid substitutions, to the CDR1, CDR2 or CDR3 region of SEQ ID NO:6, 7, or 8, and wherein an antibody or antigen-binding fragment, variant, or derivative thereof comprising the VH and VL can specifically or preferentially bind to CD20.

In some embodiments, the anti-CD20 antibody or antigen-binding fragment, variant, or derivative thereof comprises the VH CDR1, CDR2, and CDR3 region of sequences SEQ ID NO: 1, 2, and 3, and the VL CDR1, CDR2, and CDR3 region of sequences SEQ ID NO:6, 7, and 8.

In another embodiment, an isolated antibody or antigen-binding fragment, variant, or derivative thereof comprises, consists essentially of, or consists of a VH domain and a VL domain, wherein the VH has an amino acid sequence that is at least 80%, 85%, 90%, 91%, 92%, 93%, 94%, 95%, 96%, 97%, 98%, 99%, or 100% identical to a VH amino acid sequence of SEQ ID NO:4, wherein the VL domain that has an amino acid sequence that is at least 80%, 85%, 90%, 91%, 92%, 93%, 94%, 95%, 96%, 97%, 98%, 99%, or 100% identical to a VL amino acid sequence of SEQ ID NO:9, and wherein an antibody or antigen-binding fragment, variant, or derivative thereof comprising the VH domain and VL domain can specifically or preferentially bind to CD20.

In some embodiments, the anti-CD20 antibody or antigen-binding fragment thereof comprises the VH of SEQ ID NO:4 and the VL of SEQ ID NO:9.

In some embodiments, the anti-CD20 antibody or antigen-binding fragment thereof binds to the same epitope as an antibody comprising the VH of SEQ ID NO:4 and the VL of SEQ ID NO:9.

In another embodiment, an isolated antibody or antigen-binding fragment, variant, or derivative thereof comprises, consists essentially of, or consists of a heavy chain and a light chain, wherein the heavy chain has an amino acid sequence that is at least 80%, 85%, 90%, 91%, 92%, 93%, 94%, 95%, 96%, 97%, 98%, 99%, or 100% identical to a heavy chain amino acid sequence comprising SEQ ID NOs: 4 and 5, wherein the light chain has an amino acid sequence that is at least 80%, 85%, 90%, 91%, 92%, 93%, 94%, 95%, 96%, 97%, 98%, 99%, or 100% identical to a light chain amino acid sequence comprising SEQ ID NOs: 9 and 10, and wherein an antibody or antigen-binding fragment, variant, or derivative thereof comprising the heavy chain and light chain can specifically or preferentially bind to CD20.

In some embodiments, the anti-CD20 antibody or antigen-binding fragment thereof comprises a heavy chain comprising SEQ ID NOs: 4 and 5 and a light chain comprising SEQ ID NOs: 9 and 10.

In some embodiments, the anti-CD20 antibody or antigen-binding fragment thereof binds to the same epitope as an antibody comprising SEQ ID NO:4 and SEQ ID NO:5.

In some embodiments, the anti-CD20 antibody is ublituximab.

In some embodiments, the anti-CD20 antibody is EMAB603 (see WO2006/064121, which is herein incorporated by reference in its entirety), produced by the clone R603-12D11, and deposited to the Collection Nationale des Cultures de Microorganismes under the accession number CNCM I-3529.

In some embodiments, the anti-CD20 antibody is produced in the rat hybridoma YB2/0 cell line (cell YB2/3HL.P2.G11.16Ag.20, registered at the American Type Culture Collection under ATCC number CRL-1662).

The precise chemical structure of an antibody capable of specifically binding CD20 and retaining the desired activity depends on a number of factors. As ionizable amino and carboxyl groups are present in the molecule, a particular polypeptide can be obtained as an acidic or basic salt, or in neutral form. All such preparations that retain their biological activity when placed in suitable environmental conditions are included in the definition of anti-CD20 antibodies as used herein. Further, the primary amino acid sequence of the antibody can be augmented by derivatization using sugar moieties (glycosylation) or by other supplementary molecules such as lipids, phosphate, acetyl groups and the like. It can also be augmented by conjugation with saccharides. Certain aspects of such augmentation are accomplished through post-translational processing systems of the producing host; other such modifications can be introduced in vitro. In any event, such modifications are included in the definition of an anti-CD20 antibody used herein so long as the desired properties of the anti-CD20 antibody are not destroyed. It is expected that such modifications can quantitatively or qualitatively affect the activity, either by enhancing or diminishing the activity of the polypeptide, in the various assays. Further, individual amino acid residues in the chain can be modified by oxidation, reduction, or other derivatization, and the polypeptide can be cleaved to obtain fragments that retain activity. Such alterations that do not destroy the desired properties (e.g., binding specificity for CD20) do not remove the polypeptide sequence from the definition of anti-CD20 antibodies of interest as used herein.

The art provides substantial guidance regarding the preparation and use of polypeptide variants. In preparing variants of an anti-CD20 binding molecule, e.g., an antibody or antigen-binding fragment, variant, or derivative thereof, one of skill in the art can readily determine which modifications to the native protein's nucleotide or amino acid sequence will result in a variant that is suitable for use as a therapeutically active component of a pharmaceutical composition.

It is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity) . Following mutagenesis, the encoded protein can routinely be expressed and the functional and/or biological activity of the encoded protein, (e.g., ability to immunospecifically bind at least one epitope of a CD20 polypeptide) can be determined using techniques described herein or by routinely modifying techniques known in the art.

In certain embodiments, the anti-CD20 antibodies comprise at least one optimized complementarity-determining region (CDR). By "optimized CDR" is intended that the CDR has been modified and optimized sequences selected based on the sustained or improved binding affinity and/or anti-CD20 activity that is imparted to an anti-CD20 antibody comprising the optimized CDR. "Anti-CD20 activity" can include, e.g., activity which modulates one or more of the following activities associated with CD20, e.g., the ability to induce apoptosis of B-cells, the ability to induce ADCC against B-cells (e.g., CLL cells), the ability to inhibit NF-kappaB activity, the ability to inhibit Snail expression, the ability to de-repress RKIP, the ability to de-repress PTEN, the ability to sensitize a tumor cell to TRAIL-apoptosis or any other activity associated with CD20. Such activities are described, for example, in Baritaki, S. et al., *Int. J. Oncol.* 38: 1683-1694 (2011), which is herein incorporated by reference in its entirety. The modifications can involve replacement of amino acid residues within the CDR such that an anti-CD20 antibody retains specificity for the CD20 antigen and has improved binding affinity and/or improved anti-CD20 activity.

In certain anti-CD20 antibodies, or antigen-binding fragments thereof, at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain anti-CD20 antibodies or antigen-binding fragments thereof, the Fc portion can be mutated to decrease effector function using techniques known in the art. For example, modifications of the constant region can be used to modify disulfide linkages or oligosaccharide moieties that allow for enhanced localization due to increased antigen specificity or antibody flexibility. The resulting physiological profile, bioavailability and other biochemical effects of the modifications can easily be measured and quantified using well know immunological techniques without undue experimentation.

In certain embodiments, an anti-CD20 antibody or antigen-binding fragment thereof will not elicit a deleterious immune response in the animal to be treated, e.g., in a human. In one embodiment, anti-CD20 antibodies or antigen-binding fragments thereof can be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

Modified forms of antibodies or antigen-binding fragments thereof can be made from whole precursor or parent antibodies using techniques known in the art.

Anti-CD20 antibodies or antigen-binding fragments thereof can be made or manufactured using techniques that are known in the art. In certain embodiments, antibody molecules or fragments thereof are "recombinantly produced," i.e., are produced using recombinant DNA technology. Anti-CD20 antibodies or fragments thereof can be generated by any suitable method known in the art including generation of polyclonal antibodies or preparation of monoclonal antibodies, e.g., through hybridoma or phage display.

A variety of host-expression vector systems can be utilized to express antibody molecules. The host cell can be co-transfected with two expression vectors, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The host cell can also be transfected with a single vector encoding a heavy chain derived polypeptide and a light chain derived polypeptide. The coding sequences for the heavy and light chains can comprise cDNA or genomic DNA.

The expression vector or vectors can be transferred to a host cell by conventional techniques and the transfected cells are then cultured by conventional techniques to produce an antibody. Thus, host cells containing a polynucleotide encoding an antibody, or a heavy or light chain thereof, operably linked to a heterologous promoter are provided. In certain embodiments for the expression of double-chained antibodies, vectors encoding both the heavy and light chains can be co-expressed in the host cell for expression of the entire immunoglobulin molecule.

Host-expression systems represent vehicles by which the coding sequences of interest can be produced and subsequently purified, but also represent cells which can, when transformed or transfected with the appropriate nucleotide coding sequences, express a CD20 antibody in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or eukaryotic cells, e.g., for the expression of whole recombinant antibody molecules, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., *Bio/Technology* 8:2 (1990)). In some embodiments, the anti-CD20 antibody is produced in a host cell that is not a CHO cell.

Once an antibody has been recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

In some embodiments, the anti-CD20 antibody is produced by a rat hybridoma cell line. In some embodiments, the anti-CD20 antibody is produced in YB2/0 (ATCC CRL-1662)

In some embodiments, the anti-CD20 antibody is ublituximab and it is administered at a dose from: about 450 mg to about 1200 mg, about 600 to about 1200 mg, about 600 to about 1000 mg, about 600 to about 900 mg, about 600 mg, about 700 mg, about 800 mg, or about 900 mg about twice every week, about once every 1 to 9 weeks, about once every week, about twice every week, about once every 2 weeks, about once every 3 weeks, about once every 4 weeks, about once every 5 weeks, about once every 6 weeks, about once every 7 weeks, about once every 8 week, or about once every 9 weeks. In a preferred embodiment, the ublituximab is administered at a dose of about 900 mg about once every 1 to 9 weeks.

Inhibitors of Bruton's Tyrosine Kinase (BTK)

BTK is a member of the Tec family of non-receptor tyrosine kinases and is a key signaling enzyme expressed in all hematopoietic cells types except T lymphocytes and natural killer (NK) cells. BTK is a key component of the B-cell signaling pathway linking cell surface B-cell receptor (BCR) stimulation to downstream intracellular responses. BTK regulates B-cell development, activation, signaling, and survival (Kurosaki, T., *Curr Op Imm* 12:276-281 (2000); Schaeffer, E. M. and Schwartzberg, P. L., *Curr Op Imm* 12: 282-288 (2000)). In addition, BTK plays a role in a number of other hematopoetic cell signaling pathways, e.g., Toll like receptor (TLR) and cytokine receptor-mediated TNF-alpha production in macrophages, IgE receptor (FcepsilonRI) signaling in mast cells, inhibition of Fas/APO-1 apoptotic signaling in B-lineage lymphoid cells, and collagen-stimulated platelet aggregation. See, e.g., Jeffries, C. A. et al., *J Biol. Chem.* 278:26258-26264 (2003); Horwood, N. J. et al., *The Journal of Experimental Medicine* 197:1603-1611 (2003); Iwaki, S. et al., *J Biol. Chem.* 280:40261-40270 (2005); Vassilev, A. et al., *J. Biol. Chem.* 274:1646-1656 (1999), and Quek, L. S. et al., *Current Biology* 8:1137-1140 (1998). BTK functions as an important regulator of cell proliferation and cell survival in various B-cell malignancies.

In some embodiments, the BTK inhibitor is selected from the group consisting of 1-[(3R)-3-[4-Amino-3-(4-phenoxyphenyl)-1H-pyrazolo[3,4-d]pyrimidin-1-yl]piperidin-1-yl]prop-2-en-1-one (Imbruvica®, ibrutinib, or PCI-32765); 1-(R)-3-[4-amino-3-(4-phenoxyphenyl)-1H-pyrazolo[3,4-d]pyrimidin-1-yl]piperidin-1-yl]-2,3-dihydroxypropan-1-one (PCI-45227); 4-{8-Amino-3-[(2S)-1-(2-butynoyl)-2-pyrrolidinyl]imidazo[1,5-a]pyrazin-1-yl}-N-(2-pyridinyl)benzamide (acalabrutinib or ACP-196); (R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide (GDC-0834); (S)-9-(1-acryloylpiperidin-3-yl)-6-amino-7-(4-phenoxyphenyl)-7,9-dihydro-8H-purin-8-one (ONO-4059 or GS-4059); 6-cyclopropyl-8-fluoro-2-[2-(hydroxymethyl)-3-[1-methyl-5-[[5-(4-methylpiperazin-1-yl)pyridin-2-yl]amino]-6-oxopyridin-3-yl]phenyl]isoquinolin-1-one (RN-486); N-(3-((5-fluoro-2-((4-(2-methoxyethoxy)phenyl)amino)pyrimidin-4-yl)amino)phenyl)acrylamide (spebrutinib or AVL-292 or CC-292); SNS-062, as developed by Sunesis Pharmaceuticals and Biogen, see, Binnerts, M. E. et al., 2015 AACR-NCI-EORTC International Conference on Molecular Targets and Cancer Therapeutics, Boston, Mass., Nov. 8, 2015); N-(3-((2-((4-(4-methylpiperazin-1-yl)phenyl)amino)thieno[3,2-d]pyrimidin-4-yl)oxy)phenyl)acrylamide (HM-71224); 4-(tert-butyl)-N-(3-(8-(phenylamino)imidazo[1,2-a]pyrazin-6-yl)phenyl)benzamide (CGI-560); N-[3-[4,5-dihydro-4-methyl-6-[[4-(4-morpholinylcarbonyl)phenyl]amino]-5-oxopyrazinyl]-2-methylphenyl]-4-(1,1-dimethylethyl)-benzamide (CGI-1746); 4-(4-((4-((3-acrylamidophenyl)amino)-5-fluoropyrimidin-2-yl)amino)phenoxy)-N-methylpicolinamide (CNX-774); 7-benzyl-1-(3-(piperidin-1-yl)propyl)-2-(4-(pyridin-4-yl)phenyl)-1H-imidazo[4,5-g]quinoxalin-6(5H)-one (CTA-056); α-Cyano-β-hydroxy-β-methyl-N-(2,5-dibromophenyl)propenamide (LFM-A13); N-(2-chloro-6-methylphenyl)-2-[[6-[4-(2-hydroxyethyl)piperazin-1-yl]-2-methylpyrimidin-4-yl]amino]-1,3-thiazole-5-carboxamide (Sprycel® or Dasatinib or BMS-354825); BGB-3111, as developed by Beigene Co. Ltd., see, Tam, C. et al., Abstract #832, Am. Society Hematology (ASH) Annual Meeting, Orlando, Fla., Dec. 5-8, 2015); ONO-WG-307, as developed by Ono Pharmaceuticals, see, Kozaki, R. et al., *Cancer Res* 72(8 Suppl):Abstract No. 857 (2012); Yasuhiro, T. et al., *Cancer Res* 72(8 Suppl):Abstract No. 2021 (2012); JTE-051, as developed by Japan Tobacco Inc.; AVL-263 or CC-263, as developed by Avila Therapeutics/Celgene Corporation; AVL-291 or CC-291 and AVL-101 or CC-101, as developed by Avila Therapeutics/Celgene Corporation, see, Evans, E. et al., Paper presented at the 100th AACR Annual Meeting; Apr. 18-22, 2009; Denver, Colo.; see also D'Cruz, O. J. et al., *Onco Targets Ther.* 6: 161-176 (2013); TP-4207, as developed by Tolero Pharmaceuticals, Inc.; PCI-45292, as developed by Pharmacyclics, Inc., see, Chang, B. Y. et al., *Arthritis Rheum* 62:Suppl. 10, Abstract No. 286 (2010); Pan, Z. et al., *Chem Med Chem* 2:58-61 (2007); PCI-45466, as developed by Pharmacyclics, Inc., see, U.S. Patent Appl. Publ. 2016/0038495; CG-036806, as developed by Crystal Genomics; TAS-5567, as developed by Taiho Oncology, see, Kawagishi, A. et al., *Mol Cancer Ther* 12(11 Suppl)(2013): A274 and Irie, H. et al., *Mol Cancer Ther* 12(11 Suppl): A273 (2013); PCI-45261, as developed by Pharmacyclics, Inc.; KBP-7536, as developed by KBP BioSciences, see, e.g., U.S. Patent Appl. Publ. 2015/0267261; HCl-1684, as developed by Huntsman Cancer Institute, see, Bearss, D. J. et al., *Cancer Res* 71(8 Suppl):Abstract No. 2788 (2011); PLS-123, as developed by Peking University Cancer Hospital, see, Ding, N. et al., *Oncotarget* 6: 15122-15136 (April 2015); BMS-488516, as developed by Bristol-Myers Squibb, see, Lin, T. A. et al., *Biochemistry* 43:11056-11062 (2004); Won, J. et al., *International Reviews of Immunology* 27:19-41 (2008); BMS-509744, as developed by Bristol-Myers Squibb, see, Lin, T. A. et al., *Biochemistry* 43:11056-11062 (2004); Won, J. et al., *International Reviews of Immunology* 27:19-41 (2008); Benzamide, N-[5-[[5-[(4-acetyl-1-piperazinyl)carbonyl]-4-methoxy-2-methylphenyl]thio]-2-thiazolyl]-4-[[(1,2-dimethylpropyl)amino]methyl]- (HY-11066, CTK4I7891, HMS3265G21, HMS3265G22, HMS3265H21, HMS3265H22, CAS No. 439574-61-5, AG-F-54930).

In some embodiments, the BTK inhibitor is 4-{8-Amino-3-[(2S)-1-(2-butynoyl)-2-pyrrolidinyl]imidazo[1,5-a]pyrazin-1-yl}-N-(2-pyridinyl)benzamide (acalabrutinib or ACP-196).

In some embodiments, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one (ibrutinib). See, Imbruvica® full prescribing information (Pharmacyclics LLC and Janssen Biotech, Inc.). Also, see Honigsberg, L. A. et al., *PNAS* 107:13075-13080 (2010) and U.S. Pat. Nos. 7,514,444, 8,697,711, 8,703,780, 8,088,309, and 8,088,781.

In some embodiments, the ibrutinib is administered once daily at a dosage from: about 200 to about 800 mg, about 400 to about 600 mg, about 400 mg, about 420 mg, about 440 mg, about 480 mg, about 500 mg, about 520 mg, about 540 mg, about 560 mg, about 580 mg, or about 600 mg.

In some embodiments, the ibrutinib is administered once daily at a dosage of about 420 mg or about 560 mg per day. In some embodiments, the ibrutinib is administered once daily at a dosage of about 420 mg per day. In some embodiments, the ibrutinib is administered once daily at a dosage of about 560 mg per day.

Methods of Treating B-Cell Proliferative Disorders, Such as B-Cell Malignancies

In some embodiments, the B-cell population whose proliferation is to inhibited is in a human subject. In some embodiments, the human subject has a disease or disorder associated with excessive B-cell proliferation. In some embodiments, the disease associated with excessive B-cell proliferation is cancer. In some embodiments, a human subject has cancer. In some embodiments, the cancer is a hematological malignancy. In certain embodiments, the hematological malignancy is lymphoma, leukemia, or myeloma.

In some embodiments, the hematological malignancy is selected from the group consisting of acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), including extranodal and nodal MZL, hairy cell leukemia (HCL), Burkitt's lymphoma (BL), and Richter's transformation.

In some embodiments, the hematological malignancy is selected from the group consisting of chronic lymphocytic leukemia (CLL), small lymphocytic lymphoma (SLL), non-Hodgkin's lymphoma (NHL), mantle cell lymphoma (MCL), follicular lymphoma (FL), diffuse large B-cell lymphoma (DLBCL), and marginal zone lymphoma (MZL).

In some embodiments, the cancer overexpresses CD20.

In some embodiments, the cancer is refractory to chemotherapy.

In some embodiments, the cancer is refractory to non-TGR-1202 P13K-delta inhibitors.

In some embodiments, the cancer is refractory to non-ublituximab anti-CD20 antibodies.

In some embodiments, the cancer is refractory to any agent described herein, i.e., an anti-CD20 antibody, a P13K delta selective inhibitor, or a BTK inhibitor, when said agent was administered individually to a subject (i.e, used as a monotherapy).

In some embodiments, the cancer is refractory to a BTK inhibitor. In some embodiments, the cancer is refractory to ibrutinib.

In some embodiments, the cancer is refractory to rituximab.

In some embodiments, the cancer has relapsed.

In some embodiments, the human subject has one or more genetic mutations selected from the group consisting of 17p del, 11q del, p53, unmutated IgVH together with ZAP-70+ and/or CD38+, and trisomy 12.

Administration of the Combination

In some embodiments, the agents (i.e., i, ii, and iii, as described herein) to be used in combination in the methods described herein, are administered to a subject separately.

In some embodiments, the agents (i.e., i, ii, and iii) to be used in combination in the methods described herein, are administered to a subject sequentially, although, as noted below, the particular order of administration is not an issue. In some embodiments, the agents (i.e., i and iii), which will be used in combination with the anti-CD20 antibody (i.e., ii) in the methods described herein, are administered to the subject simultaneously or sequentially. In some embodiments, the agents (i.e., i and iii) are contained in the same pharmaceutical composition. In some embodiments, the agents (i.e., i and iii) are formulated for oral administration.

In some embodiments, the combination of agents is sequentially administered in induction, consolidation, and/or maintenance regimens.

In some embodiments, two of the agents i, ii, or iii, are administered together in order to induce a partial anti-tumor response, followed by administration of the third agent to enhance the anti-tumor response. In some embodiments, a complete anti-tumor response (CR) is observed following administration of all agents (e.g., i, ii, and iii, as disclosed herein) to said subject. In some embodiments, a subject administered any of the methods described herein achieves a complete response with minimal residual disease (MRD).

In some embodiments, a subject administered any of the methods described herein achieves a partial reponse (PR) when all three agents are administered in combination. In some embodiments, a subject administered any of the methods described herein achieves a partial response (PR) or a complete response (CR) that is durable for at least two months.

In some embodiments, at least one of the agents, i, ii, and/or iii, is administered in a maintenance therapy in order to keep the B-cell proliferative disorder from returning after successful treatment. In some embodiments, the agent is administered in maintenance therapy for an extended period of time, e.g., until unmanageable toxicity, or disease progression occurs. In some embodiments, the maintenance therapy ends when disease progression occurs. In some embodiments, UTX infusion continues being administered every three months until disease progression. In some embodiments, TGR-1202 single agent therapy is administered daily until disease progression. In some embodiments, ibrutinib single agent therapy is administered daily until disease progression. In some embodiments, TGR-1202 and ibrutinib therapies are administered daily until disease progression.

In some embodiments, the methods described herein further comprises administering to the subject at least one additional therapeutic agent for inhibiting B-cell proliferation. In some embodiments, the at least one additional therapeutic agent is selected from the group consisting of mitotic inhibitors, alkylating agents, anti-metabolites, anthracyclines, *vinca* alkaloids, plant alkaloids, nitrogen mustards, proteasome inhibitors, intercalating antibiotics, growth factor inhibitors, cell-cycle inhibitors, biological response modifiers, anti-hormones, angiogenesis inhibitors, anti-androgens, DNA interactive agents, purine analogues, topoisomerase I inhibitors, topoisomerase II inhibitors, tubulin interacting agents, hormonal agents, thymidilate synthase inhibitors, non-BTK and non-P13K-delta tyrosine kinase inhibitors, angiogenesis inhibitors, EGF inhibitors, VEGF inhibitors, CDK inhibitors, SRC inhibitors, c-Kit inhibitors, Her1/2 inhibitors, inhibitors of myc, anti-tumor antibodies, monoclonal antibodies directed against growth factor receptors, protein kinase modulators, radioactive isotopes, immunotherapies, glucocorticoids, and combinations thereof.

In some embodiments, the at least one additional therapeutic agent is an anti-cancer agent selected from the group consisting of DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate; other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); and other protein kinase modulators. Other anti-cancer agents that could be used in the methods and kits of the invention will be known to those skilled in the oncology art.

In some embodiments, the at least one additional therapeutic agent is selected from the group consisting of a proteasome inhibitor, Bortezomib (Velcade®), Carfilzomib (PR-171), PR-047, disulfiram, lactacystin, PS-519, eponemycin, epoxomycin, aclacinomycin, CEP-1612, MG-132, CVT-63417, PS-341, vinyl sulfone tripeptide inhibitors, ritonavir, PI-083, (+/-)-7-methylomuralide, (-)-7-methylomuralide, lenalidomide, and combinations thereof.

In some embodiments, the at least one additional therapeutic agent is a combination of chemotherapies, known to treat hematological malignancies, such as, e.g., "CHOP" (a combination including (i) cyclophosphamide such as cytoxan, (ii) doxorubicin or other topoisomerase II inhibitors such as adriamycin, (iii) vincristine or other vincas such as oncovin; and (iv) a steroid such as hydrocortisone or prednisolone); "R-CHOP" (a combination including rituxan, cyclophosphamide, doxorubicin, vincristine, and prednisone); "ICE" (a combination including ifosfamide, carboplatin, and etoposide); "R-ICE" (a combination including rituxan, ifosfamide, carboplatin, and etoposide); "R-ACVBP" (a combination of rituximab, doxorubicin, cyclophosphamide, vindesine, bleomycin and prednisone); "DA-EPOCH-R" (a combination of dose-adjusted etoposide, doxorubicin, cyclophosphamide, vincristine, prednisone and rituximab); "R-bendamustine" (a combination of bendamustine and rituximab); "GemOx or R-GemOx" (a combination of gemcitabine and oxaliplatin, with or without rituximab); and "DHAP" (a combination including dexamethasone, cytarabine, and cisplatin).

Any oncolytic agent that is routinely used in a cancer therapy context finds use in the therapeutic methods of the present disclosure. For example, the U.S. Food and Drug Administration (FDA) maintains a formulary of oncolytic agents approved for use in the United States. International counterpart agencies to the FDA maintain similar formularies. Those skilled in the art will appreciate that the "product labels" required on all U.S. approved chemotherapeutics describe approved indications, dosing information, toxicity data, and the like, for the exemplary agents.

The combination of agents comprising a P13K-delta inhibitor, an anti-CD20 antibody, and a BTK inhibitor (or more than one of any or all agents) can be administered in any order or at any interval as determined by those skilled in the art. For example, a P13K-delta inhibitor of formula A, ublituximab or an anti-CD20 antibody that binds to the same epitope as ublituximab, and a BTK inhibitor can be administered sequentially (in any order), simultaneously, or via any combination of sequential and simultaneous administrations. Any combination of a P13K-delta inhibitor of formula A, ublituximab or an anti-CD20 antibody that binds to the same epitope as ublituximab, and a BTK inhibitor can be administered in the same pharmaceutical compositions or in separate pharmaceutical compositions. For example, a P13K-delta inhibitor of formula A and a BTK inhibitor can be administered in the same pharmaceutical composition.

Administration of the combination of agents, whether simultaneous, sequential (in any order) or both, can be performed according to any number of desired intervals of minutes (e.g., 0-60 minutes), hours (e.g., 0-24 hours), days (e.g., 0-7 days), and/or weeks (e.g., 0-52 weeks), as can be decided and determined by one of skill in the art. The dosing can also vary over time, for example, starting with a once weekly dose for a period of time (e.g., for 1, 2, 3, 4, 5, or 6 weeks) followed by dosing once every two weeks, once every three weeks, once every four weeks, once every five weeks, or once every six weeks.

The P13K-delta selective inhibitor, the anti-CD20 antibody, and the BTK inhibitor that are to be used in combination in the methods of the invention can be formulated into pharmaceutical compositions for administration to mammals, including humans. The pharmaceutical compositions comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The agents to be used in combination in accordance with the methods of the invention can be administered by any suitable method, e.g., orally, parenterally, intraventricularly, by inhalation spray, topically, rectally, nasally, buccally, vaginally or via an implanted reservoir. The mode of administration for each agent does not have to be the same.

In a preferred embodiment, the P13K-delta inhibitor (e.g., TGR-1202) is administered orally.

In a preferred embodiment, the BTK inhibitor (e.g., Ibrutinib) is administered orally.

As used herein, the term "parenteral" includes subcutaneous, intravenous, intramuscular, intra-articular, intra-synovial, intrasternal, intrathecal, intrahepatic, intralesional and intracranial injection or infusion techniques. Parenteral formulations can be a single bolus dose, an infusion, or a loading bolus dose followed with a maintenance dose. These compositions can be administered at specific fixed or variable intervals, e.g., once a day, or on an "as needed" basis. In a preferred embodiment, the anti-CD20 antibody ublituximab is administered intravenously (IV), preferably by infusion.

Certain pharmaceutical compositions can be orally administered in an acceptable dosage form including, e.g., capsules, tablets, aqueous suspensions, or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

A specific dosage and treatment regimen for any particular patient will depend upon a variety of factors, including the particular therapeutic agents used, the patient's age, body weight, general health, sex, and diet, and the time of administration, rate of excretion, drug combination, and the severity of the disease being treated. In some cases, dosages may need to be modified based on scan or biopsy results. Judgment of such factors by medical caregivers is within the ordinary skill in the art. Dosage will also depend on the individual patient to be treated, the route of administration, the type of formulation, the characteristics of the compound used, tumor burden, and the desired effect. The amount used can be determined by pharmacological and pharmacokinetic principles well known in the art.

In some embodiments, the anti-CD20 antibody is ublituximab and it is administered at a dose from: about 450 mg to about 1200 mg, about 600 to about 1200 mg, about 600 to about 1000 mg, about 600 to about 900 mg, about 600 mg, about 700 mg, about 800 mg, or about 900 mg. In a preferred embodiment, the ublituximab is administered at a dose of about 900 mg.

Ublituximab may be administered about twice every week, about once every 1 to 9 weeks, about once every week, about once every 2 weeks, about once every 3 weeks, about once every 4 weeks, about once every 5 weeks, about once every 6 weeks, about once every 7 weeks, about once every 8 week, or about once every 9 weeks. One skilled in the art will appreciate that the dosage of ublituximab and/or frequency of administering ublituximab may change during the course of therapy (lowered or increased) depending upon the patient's clinical response, side effects, etc.

In some embodiments, ublituximab is administered on day 1, 8, and 15 of cycle 1 and cycle 2 and day 1 on cycles 4, 6, 9, and 12, wherein each cycle is 28 days.

In some embodiments, a P13K-delta selective inhibitor of formula A is administered once a day at a dosage from: about 200 mg to about 1200 mg, about 400 mg to about 1000 mg, about 400 mg to about 800 mg, about 400 mg, about 500 mg, about 600 mg, about 700 mg, about 800 mg, about 900 mg, about 1000 mg, or about 1200 mg.

In some embodiments, the P13K-delta selective inhibitor of formula A is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one PTSA salt (TGR-1202) and it is administered at a dose from about 400 mg to about 1200 mg per day. In some embodiments, the TGR-1202 is administered at a dose of about 400 mg per day. In some embodiments, the TGR-1202 is administered at a dose of about 600 mg per day. In some embodiments, the TGR-1202 is administered at a dose of about 800 mg per day.

In some embodiments, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one (ibrutinib). In some embodiments, the ibrutinib is administered once daily at a dosage from: about 200 to about 800 mg, about 400 to about 600 mg, about 400 mg, about 420 mg, about 440 mg, about 480 mg, about 500 mg, about 520 mg, about 540 mg, about 560 mg, about 580 mg, or about 600 mg. In some embodiments, the ibrutinib is administered at a dose of about 420 mg per day or about 560 mg per day. In some embodiments, the ibrutinib is administered at a dose of about 420 mg per day. In some embodiments, the ibrutinib is administered at a dose of about 560 mg per day. The dosages of other non-ibrutinib BTK inhibitors that can be used in the methods of the invention can be routinely determined by those skilled in the art based on the scientific/medical literature.

Supplementary active compounds can also be incorporated into the methods and kits of the present invention. For example, an anti-CD20 antibody, a P13K-delta selective inhibitor, and a BTK inhibitor can be coformulated with and/or coadministered with one or more additional therapeutic agents. As non-limiting examples, the methods and kits could be coformulated with anti-cancer agents such as DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and antimetabolites, such as methotrexate; other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); and other protein kinase modulators. The additional active agent can also be a proteasome inhibitor, Bortezomib (Velcade®), Carfilzomib (PR-171), PR-047, disulfiram, lactacystin, PS-519, eponemycin, epoxomycin, aclacinomycin, CEP-1612, MG-132, CVT-63417, PS-341, vinyl sulfone tripeptide inhibitors, ritonavir, PI-083, (+/−)-7-methylomuralide, (−)-7-methylomuralide, lenalidomide (Revlimid®), or a combination thereof.

Kits

In one aspect, provided herein is a kit comprising (a) at least one P13K-delta selective inhibitor, at least one anti-CD20 antibody, and at least one inhibitor of BTK; and (b) instruction for using a P13K-delta selective inhibitor in combination with an anti-CD20 antibody and an inhibitor of BTK.

In another aspect, provided herein is a kit comprising at least one P13K-delta selective inhibitor of formula A, at least one anti-CD20 antibody that is ublituximab or an antibody that binds to the same epitope as ublituximab, and at least one inhibitor of BTK. In some embodiments, other agents that can be used to perform the methods described herein, and combinations thereof, are included in the kit. Such kits can include, for example, other compounds and/or compositions to treat B-cell malignancies known to those skilled in the art, a device(s) for administering the compounds and/or compositions, and written instructions in a form prescribed by a governmental agency regulating the manufacture, use or sale of pharmaceuticals or biological products.

In some embodiments, a kit comprises (a) a P13K-delta selective inhibitor of formula A (e.g., TGR-1202), or a stereoisomer thereof, or a pharmaceutically acceptable salt, solvate, or prodrug thereof; ublituximab or an anti-CD20 antibody or fragment thereof that binds to the same epitope as ublituximab; and an inhibitor of BTK, and (b) instructions for using said P13K-delta selective inhibitor in combination with ublituximab or an anti-CD20 antibody or fragment thereof that binds to the same epitope as ublituximab and an inhibitor of BTK.

In some embodiments, the inhibitor of BTK in the kit is ibrutinib. In some embodiments, the inhibitor of BTK in the kit is acalabrutimib.

In some embodiments, the P13K-delta selective inhibitor in the kit is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one.

In some embodiments, the P13K-delta selective inhibitor in the kit is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one PTSA salt (TGR-1202, also known as umbralisib).

In some embodiments, the kit further comprises ublituximab or an anti-CD20 antibody or fragment thereof that binds to the same epitope as ublituximab.

In some embodiments, the kit further comprises ublituximab.

One skilled in the art will readily recognize that the disclosed combination of agents (antibodies and small molecule inhibitors) described herein for use in the methods of the invention can be readily incorporated into one of the established kit formats that are well known in the art.

Further provided are kits comprising (a) a P13K-delta selective inhibitor of formula A, an anti-CD20 antibody, a BTK inhibitor, or a combination thereof; and (b) an additional anti-cancer agent. In some embodiments, the kit comprises TGR-1202, ublituximab, and ibrutinib or another inhibitor of BTK (as described herein), and a chemotherapeutic agent selected from the group consisting of DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate; other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); and other protein kinase modulators.

Methods of Using Combinations of a P13K-Delta Selective Inhibitor of Formula a, Ublituximab or an Anti-CD20 Antibody that Binds the Same Epitope as Ublituximab, and a BTK Inhibitor Combinations of a P13K-delta selective inhibitor of Formula A, ubltuximab or an anti-CD20 antibody that binds the same epitope as ublituximab, and a BTK inhibitor can be used in methods of treating B-cell proliferative diseases (such as B-cell malignancies) in a subject.

In some embodiments, a P13K-delta selective inhibitor of Formula A can be used in the manufacture of a medicament for the treatment of a B-cell proliferative disorder, wherein the P13K-delta selective inhibitor of Formula A is to be administered in combination (e.g., sequentially or simultaneously) with an anti-CD20 antibody that is ublituximab or an antibody that binds to the same epitope as ublituximab, and a BTK inhibitor. In addition, an anti-CD20 antibody can be used in the manufacture of a medicament for the treatment of a B-cell proliferative disorder, wherein the anti-CD20 antibody is to be administered in combination (e.g., sequentially or simultaneously) with a P13K-delta selective inhibitor of Formula A and a BTK inhibitor. In some embodiments, the anti-CD20 antibody is ublituximab. In some embodiments, the P13K-delta selective inhibitor is TGR-1202. In some embodiments, the anti-CD20 antibody is ublituximab and the P13K-delta selective inhibitor is TGR-1202.

The invention further provides a method of inhibiting P13K-delta isoform and/or CD20, and/or BTK in a subject by administering to the subject an effective amount of the agents of the present invention in combination.

The invention further provides a method of treating, preventing, and/or inhibiting a P13K-delta-mediated disease, disorder or condition and/or a CD20-mediated disease, disorder, or condition (such as cancer or other proliferative disease or disorder) and/or a BTK-mediated disease, disorder, or condition in a patient by administering to the a patient an effective amount of the agents of the present invention in combination.

The invention further provides a method of treating a P13K-delta isoform- and/or CD20- or BTK-associated disease, disorder or condition in a patient by administering to the patient an effective amount of the agents of the present invention in combination. In some embodiments, the amount of the agents administered in combination is sufficient to treat a P13K-delta isoform- and/or CD20- and/or BTK-associated disease, disorder, or condition by selective inhibition of P13K-delta and/or CD20 and/or BTK.

In some embodiments, the invention further provides a method of treating a B-cell proliferative disease by administering to a patient in need of such treatment an effective amount of at least one P13K delta selective inhibitor, at least one anti-CD20 antibody, and at least one BTK inhibitor. In some embodiments, the anti-CD20 antibody is ublituximab. In some embodiments, the P13K-delta selective inhibitor is TGR-1202. In some embodiments, the BTK inhibitor is ibrutinib. In some embodiments, the anti-CD20 antibody is ublituximab and the P13K-delta selective inhibitor is TGR-1202. In some embodiments, the anti-CD20 antibody is ublituximab, the P13K-delta selective inhibitor is TGR-1202, and the BTK inhibtor is ibrutinib.

In some embodiments, the invention further provides a method of treating a B-cell proliferative disease by administering to a patient in need of such treatment an effective amount of at least one P13K delta selective inhibitor of formula A, at least one anti-CD20 antibody that is ublituximab or an antibody that binds to the same epitope as ublituximab, and at least one BTK inhibitor of the present invention. In some embodiments, the amounts of the agents administered in combination are sufficient to treat the B-cell proliferative disease by selective inhibition of P13K-delta, and/or inhibition of CD20, and/or inhibition of BTK. In some embodiments, the B-cell proliferative disorder is a B-cell malignancy (e.g., lymphoma, leukemia, or myeloma). In some embodiments, the anti-CD20 antibody is ublituximab. In some embodiments, the P13K-delta selective inhibitor is TGR-1202. In some embodiments, the BTK inhibitor is ibrutinib. In some embodiments, the anti-CD20 antibody is ublituximab and the P13K-delta selective inhibitor is TGR-1202. In some embodiments, the anti-CD20 antibody is ublituximab, the P13K-delta selective inhibitor is TGR-1202, and the BTK inhibtor is ibrutinib.

The invention further provides a method for treating a B-cell proliferative disease by administering to a patient in need of such treatment an effective amount of a combination of the agents of the present invention, in further combination (simultaneously or sequentially) with at least one other anti-cancer agent. In one embodiment, the amount of the P13K-delta selective inhibitor of Formula A administered is sufficient to treat (or facilitate treatment of) the B-cell proliferative disease by selective inhibition of P13K-delta.

The combinations of the agents of the present invention are particularly useful in the treatment of a variety of hematological cancers, such as, but not limited to, e.g., acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), hairy cell leukemia (HCL), Burkitt's lymphoma (BL), and Richter's transformation.

Those skilled in the art would appreciate that other types of lymphomas or leukemias would find use in the combination of agents of the invention, such as, e.g., B-cell prolymphocytic leukemia, lymphoplasmacytic lymphoma, plasma cell myeloma/plasmacytoma, Hodgkin's lymphoma, and Burkitt's lymphoma/Burkitt's cell leukemia.

In some embodiments, Non-Hodgkin's Lymphoma (NHL) is aggressive NHL or indolent NHL. Examples of aggressive NHL include B-cell neoplasms, diffuse large B-cell lymphoma (DLBCL), T/NK cell neoplasms, anaplastic large cell lymphoma, peripheral T-cell lymphomas, precursor B-lymphoblastic leukemia/lymphoma, precursor T-lymphoblastic leukemia/lymphoma, Burkitt's lymphoma, adult T-cell lymphoma/leukemia (HTLV 1+), primary CNS lymphoma, mantle cell lymphoma (MCL), polymorphic post-transplantation lymphoproliferative disorder (PTLD), AIDS-related lymphoma, true histiocytic lymphoma, and blastic NK-cell lymphoma. The most common type of aggressive NHL is diffuse large cell lymphoma. Non-limiting examples of indolent NHL include follicular lymphoma, small lymphocytic lymphoma, marginal zone lymphoma (such as extranodal marginal zone lymphoma (also called mucosa associated lymphoid tissue—MALT lymphoma), nodal marginal zone B-cell lymphoma (monocytoid B-cell lymphoma), splenic marginal zone lymphoma), and lymphoplasmacytic lymphoma (Waldenstrom's macroglobulinemia). In some embodiments, a subject has aggressive NHL or indolent NHL.

In some embodiments, a patient has a condition selected from the group consisting of mantle cell lymphoma (MCL), diffuse large B cell lymphoma (DLBCL), follicular lymphoma (FL), acute lymphocytic leukemia (ALL), acute myeloid leukemia (AML), chronic lymphocytic leukemia (CLL), small lymphocytic lymphoma (SLL), multiple myeloma (MM), and marginal zone lymphoma.

The combination of agents of the present invention as modulators of apoptosis are useful in the treatment, prevention, and inhibition of cancer (including, but not limited to, the types of B-cell malignancies mentioned above).

The combination of agents of the present invention are also useful in the chemoprevention of cancer. Chemoprevention involves inhibiting the development of invasive cancer by blocking the initiating mutagenic event, blocking the progression of pre-malignant cells that have already suffered an insult, or inhibiting tumor relapse. The compounds are also useful in inhibiting tumor angiogenesis and metastasis. One embodiment of the invention is a method of inhibiting tumor angiogenesis or metastasis in a patient by administering an effective amount of one or more compounds of the present invention.

In the aforementioned methods of treatment, one or more additional therapeutic agents can be administered with the combination of agents of the present invention. For example, the combination of agents of the present invention are useful in combining (administered together or sequentially) with known anti-cancer treatments such as radiation therapy or with one or more cytostatic, cytotoxic or anticancer agents, such as, for example, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidylate synthase inhibitors, such as 5-fluorouracil; and anti-metabolites, such as methotrexate; other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); and other protein kinase modulators. The additional active agent can also be a proteasome inhibitor, Bortezomib (Velcade®), Carfilzomib (PR-171), PR-047, disulfiram, lactacystin, PS-519, eponemycin, epoxomycin, aclacinomycin, CEP-1612, MG-132, CVT-63417, PS-341, vinyl sulfone tripeptide inhibitors, ritonavir, PI-083, (+/−)-7-methylomuralide, (−)-7-methylomuralide, lenalidomide (Revlimid®), or a combination thereof.

The combination of agents of the present invention are also useful in combining (administered together or sequentially) with one or more steroidal anti-inflammatory drugs (e.g, prednisone or prednisolone), non-steroidal anti-inflammatory drugs (NSAIDs) or immune selective anti-inflammatory derivatives (ImSAIDs).

In some embodiments, a patient has a relapsed or refractory condition (i.e., B-cell cancer). In some embodiments, the subject is refractory to chemotherapy treatment, or in relapse after treatment with chemotherapy. In some embodiments, the subject is refractory to a non-TGR-1202 P13K-delta inhibitor. In some embodiments, the subject is refractory to an agent (i, ii, or iii) described herein, where the agent was administered individually (i.e., as a monotherapy).

In some embodiments, the cancer is resistant to treatment with rituximab. In some embodiments, the cancer shows a reduced response to treatment with rituximab. In some embodiments, the subject has previously been treated with rituximab.

In a particular embodiment, the methods comprise reducing the level of NF-kappa-B activity, reducing SNAIL expression, increasing RKIP activity, increasing PTEN activity, increasing tumor sensitivity to TRAIL-apoptosis, reducing the level of P13K-delta activity or a combination thereof in a subject.

In a particular embodiment, the combination of the P13K-delta inhibitor of formula A, the anti-CD20 antibody ublituximab, and the BTK inhibitor, as described herein, depletes B-cells from human whole blood. In some embodiments, the described triplet combination depletes B-cells from human whole blood to a greater extent than either the P13K-delta inhibitor of formula A, the anti-CD20 antibody ublituximab, or the BTK inhibitor alone depletes B-cells from human whole blood. In some embodiments, the combination of the P13K-delta inhibitor of formula A, the anti-CD20 antibody ublituximab, and the BTK inhibitor depletes B-cells from human whole blood to a greater extent than the sum of the depletion by the P13K-delta inhibitor of formula A, the depletion by the anti-CD20 antibody ublituximab, and the depletion by the BTK inhibitor.

In some embodiments, a P13K-delta inhibitor of formula A, the anti-CD20 antibody, and the BTK inhibitor are used in a method of treating a disease or disorder associated with excessive B-cell proliferation, wherein the method comprises administration of a P13K-delta inhibitor of formula A, the anti-CD20 antibody ublituximab, and the BTK inhibitor to a subject in need thereof. In some embodiments, a P13K-delta inhibitor of formula A, the anti-CD20 antibody, and the BTK inhibitor are used in a method of treating a disease or disorder associated with excessive B-cell activity, wherein the method comprises administration of a P13K-delta inhibitor of formula A, the anti-CD20 antibody, and the BTK inhibitor to a subject in need thereof. In some embodiments, a P13K-delta inhibitor of formula A, the anti-CD20 antibody, and the BTK inhibitor are used in a method of treating a disease or disorder associated with excessive number of B-cells, wherein the method comprises administration of a P13K-delta inhibitor of formula A, the anti-CD20 antibody, and the BTK inhibitor to a subject in need thereof. In some embodiments, the anti-CD20 antibody is ublituximab. In some embodiments, the P13K-delta selective inhibitor is TGR-1202. In some embodiments, the BTK inhibitor is ibrutinib. In some embodiments, the anti-CD20 antibody is ublituximab and the P13K-delta selective inhibitor is TGR-1202. In some embodiments, the anti-CD20 antibody is ublituximab, the P13K-delta selective inhibitor is TGR-1202, and the BTK inhibtor is ibrutinib.

When the agents of the present disclosure are administered to a subject (e.g., a human subject), the agents can be administered as a composition that comprises a pharmaceutically acceptable carrier or excipient, by any appropriate route, such as intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical. Delivery can be either local or systemic. Pharmaceutical compositions can take the form of solutions, suspensions, emulsions, tablets, pills, pellets, powders, multi-particulates, capsules, capsules containing liquids, capsules containing powders, capsules containing multi-particulates, lozenges, sustained-release formulations, suppositories, transmucosal films, sublingual tablets or tabs, aerosols, sprays, or any other form suitable for use. In one embodiment, the composition is in the form of a tablet. In another embodiment, the composition is in the form of a capsule. Other examples of suitable pharmaceutical excipients are described in *Remington's Pharmaceutical Sciences* 1447-1676 (Alfonso R. Gennaro ed., 19th ed. 1995), incorporated herein by reference in its entirety.

In certain embodiments, the agents of the present disclosure are formulated for oral administration in the form of tablets, capsules, gelcaps, caplets, lozenges, aqueous or oily solutions, suspensions, granules, powders, emulsions, syrups, or elixirs, for example. The tablets can be compressed, enteric-coated, sugar-coated, film-coated, multiply compressed or multiply layered.

In certain embodiments, the agents of the present disclosure are formulated into a pharmaceutical composition for intravenous administration. Typically, such compositions comprise sterile isotonic aqueous buffer. Where necessary, the compositions can also include a solubilizing agent. Generally, the ingredients are supplied either separately or mixed together in unit dosage form, for example, as a dry lyophilized powder or water free concentrate in a hermetically sealed container such as an ampule or sachette indicating the quantity of active agent. Where administered by infusion, the compositions can be dispensed, for example, with an infusion bottle containing sterile pharmaceutical grade water or saline. Where administered by injection, an ampule of sterile water for injection or saline can be provided so that the ingredients can be mixed prior to administration.

EXAMPLES

Example 1: Triple Combination of a P13K-Delta Inhibitor of Formula a (TGR-1202), an Anti-CD20 Antibody (Ublituximab), and a BTK Inhibitor (Ibrutinib) to Treat B-Cell Malignancies Background:

Novel targeted agents are emerging for B-cell malignancies, but few studies have successfully and safely combined these agents. Ublituximab (UTX) is a novel glycoengineered type 1 chimeric IgG1 mAb targeting a unique epitope on the CD20 antigen that is not targeted by rituximab or ofatumumab. See, Miller, J. et al., *Blood* 120: Abstract No. 2756 (2012); Deng, C. et. al., *J. Clin. Oncol.* 31:Abstract No. 8575 (2013); O'Connor, O. A. et al., *J. Clin. Oncol.* 32:5s (2014), (suppl; Abstract No. 8524). Ublituximab was glycoengineered for potent activity, exhibiting a unique primary amino acid sequence and a low fucose content, which was designed to induce superior antibody-dependent cell-mediated cytotoxicity ("ADCC"). Responses with single agent ublituximab have been observed in rituximab refractory patients. Id.

Umbralisib (also known as TGR-1202) is a next generation, highly specific, once daily, orally available, P13K-delta inhibitor, active in patients with a wide variety of relapsed or refractory (rel/ref) hematologic malignancies. See, O'Connor, O. A. et al., *Blood* 126: Abstract No. 4154 (2015); Burris, H. et al., *J Clin Oncol* 33 (2015) (suppl; abstract 7069); Burris, H et al., *J Clin Oncol* 32:5s, (2014) (suppl; abstract 2513); Burris. H. et al., *Blood* 124: Abstract No. 1984 (2014). TGR-1202 has a unique molecular structure that provides it with an advantageous safety profile, notably with respect to hepatic toxicity and colitis. Id. The favorable safety profile of TGR-1202 compared to prior inhibitors has been demonstrated, including in long-term follow up. Burris, H. et al., "Long-term follow-up of the PI3K delta inhibitor TGR-1202 demonstrates a differentiated safety profile and high response rates in CLL and NHL: Integrated-analysis of TGR-1202 monotherapy and combined with ublituximab," American Society of Clinical Oncology Annual Meeting (ASCO). Abstract #7512 (Jun. 3, 2016). The delta isoform of P13K is highly expressed in cells of hematopoietic origin, and strongly upregulated, and often mutated, in various hematologic malignancies.

The orally-administered BTK inhibitor ibrutinib is currently FDA-approved and marketed under the name Imbruvica® for the treatment of a variety of B-cell neoplasms, such as mantle cell lymphoma, CLL, and Waldenstrom's macroglobulinemia (a form of non-Hodgkin's lymphoma (NHL)). See, Imbruvica® full prescribing information (Pharmacyclics LLC and Janssen Biotech, Inc.). Also, see Honigsberg, L. A. et al., *PNAS* 107:13075-13080 (2010) and U.S. Pat. Nos. 7,514,444, 8,697,711, 8,703,780, 8,088,309, and 8,088,781.

The safety, maximum tolerated dose (MTD), and efficacy of the triplet combination of the anti-CD20 antibody, ublituximab, +the PI3K-delta inhibitor, TGR-1202, +the BTK inhibitor, ibrutinib, were evaluated in 38 patients with relapsed and refractory B-cell malignancies, such as chronic lymphocytic leukemia (CLL) and Non-Hodgkins Lymphoma (NHL) in a Phase 1 clinical trial.

Methods:

Patients eligible for the trial had a confirmed diagnosis of chronic lymphocytic leukemia (CLL), small lymphocytic lymphoma (SLL), or B-cell non-Hodgkin lymphoma (NHL) with an Eastern Cooperative Oncology Group (ECOG) performance status (PS)≤2, and adequate organ system function (i.e., ANC≥500/µl; platelets≥30K/µl). In general, patients had to have relapsed after, or were refractory to, at least one prior treatment regimen, with no limit on the number of prior therapies. (One exception was treatment naïve CLL/SLL patients). Patients with other B-cell lymphoproliferative disorders (i.e., Richter's Transformation), or patients that were refractory (did not respond) to prior P13K-delta inhibitors or prior BTK inhibtors were also eligible. Patients that relapsed from prior autologous stem cell transplant after 90 days were also eligible.

A total of 38 patients (n=38) were administered the triplet combination, including 6 patients with follicular lymphoma (FL), 16 patients with chronic lymphocytic leukemia (CLL), 4 patients with small lymphocytic lymphoma (SLL), 6 patients with diffuse large B-cell lymphoma (DLBCL), 2 patients with marginal zone lymphoma (MZL), and 4 patients with mantle cell lymphoma (MCL). The median patient age was 65 years (range 32-85). The 29 male and 9 female patients had received a median of 3 prior treatment regimens (range 0-6). The number of patients with 3 or more prior therapies was 21 (55%). Regarding the ECOG scale of performance status for the 38 patients studied: 14 patients were at ECOG 0; 21 patients were at ECOG 1; and 3 patients were at ECOG 2. See, Oken, M. M. et al., *Am J Clin. Oncol.* 5:649-655 (1982). Thirteen patients (34%) were refractory to immediate prior therapy and 15 patients were refractory to rituximab (39%).

Three cohorts (cohorts 1, 2, and 3) for patients with CLL and SLL and three cohorts (cohorts 1, 2, and 3) for patients with NHL (which included subtypes FL, DLBCL, MZL, and MCL) were evaluated independently in a dose escalation design to evaluate safety and dose limiting toxicities (DLT). The three cohorts for each CLL and NHL group of patients were evaluated with TGR-1202 dose escalation starting with micronized doses of 400 mg (cohort 1), followed by 600 mg (cohort 2), and 800 mg (cohort 3). TGR-1202 was administered once a day in combination with ibrutinib, which was administered once a day at 420 mg (for CLL patients) and 560 mg (for NHL patients). Both TGR-1202 and ibrutinib were administered once daily beginning on day 1 of cycle 1. See, FIG. 1.

Ublituximab (UTX), however, was not administered daily. UTX was administered to patients by intravenous infusion at a dose of 900 mg on days 1, 8, and 15 of cycle 1 and day 1 of cycles 2, 3, 4, 5, 6, 9, and 12. Each cycle was 28 days. Scans were performed at week 8 and every 12 weeks thereafter to assess efficacy. After month 12, all patients continued on both TGR-1202 and ibrutinib daily therapy. See, FIG. 1.

Results:

Safety and Tolerability

Thirty-eight (38) patients were evaluable for safety. UTX in combination with TGR-1202 and ibrutinib was well-tolerated in the 38 patients at dose levels of TGR-1202 up through 800 mg, the highest dose level tested to date in the study. The most frequently reported adverse events (AE), reported by 47% of patients, were diarrhea and fatigue, with only one Grade 3 or 4 event of diarrhea reported. Other adverse events were reported as follows: dizziness (37%), with one Grade 3 or 4 event; insomnia and nausea (34%); neutropenia, cough, and infusion related reaction (IRR) (32%), with 7 patients (18%) experiencing a grade 3 or 4 neutropenia; thrombocytopenia (29%), with 3 patients (8%) experiencing a grade 3 or 4 event; pyrexia and rash (29%), with one Grade 3 or 4 event in each; anemia (26%), with one Grade 3 or 4 event; sinusitis (24%); dyspnea and stomatitis (21%), with one Grade 3 or 4 event in each, and pneumonia (18%) with 11% experiencing a Grade 3 or 4 event. Pneumonia and neutropenia were the only Grade 3 or 4 adverse events in greater than 10% of patients.

Of the 38 patients treated to date, two patients discontinued due to an adverse event (pneumonia and sepsis). One dose limiting toxicity (DLT) was observed in the CLL level 1 cohort (400 mg TGR-1202) due to reactivation of varicella zoster. No other DLT's were observed.

Clinical Activity

Thirty six (36) of 38 patients were evaluable for efficacy (two patients discontinued prior to the first efficacy assessment—1 patient was removed per investigator discretion and 1 patient was removed due to pneumonia). The efficacy of treating CLL was examined per the standard international working group guidelines set forth in Hallek, M. et al., *Blood* 111:5446-5456 (2008). The efficacy of treating NHL was examined per the standard international working group guidelines set forth in Cheson, B. D. et al., *J Clin Oncol* 25:579-586 (2007).

A clinical response was observed at all three dose levels of TGR-1202.

FIG. 2 is a bar graph depicting efficacy as reflected in the best percent change from baseline in disease burden in all patients who had received at least one post baseline scan to assess disease/tumor burden. FIG. 4 presents efficacy results in terms of the level of clinical response (i.e., CR, PR, ORR, SD, and PD).

In the CLL/SLL cohort, 100% of patients (19 of 19) achieved an objective response, with 8 out of 16 CLL patients having a 17p and/or 11q deletion (a high risk feature). See, FIGS. 2 and 4. Three CLL patients had prior BTK and/or P13K-delta inhibitor therapy, including one patient refractory to both idelalisib and ibrutinib who attained a complete response that has been ongoing for 1.5 years.

The two patients with marginal zone lymphoma (MZL) achieved an objective response with one being a complete response (CR) and one being a partial response (PR). See, FIGS. 2 and 4.

In the 5 patients with heavily pre-treated (≥4 prior lines of therapy) follicular lymphoma (FL), 80% (4 of 5) achieved an objective response including 2 with prior autologous stem cell transplantation (ASCT), 1 refractory to prior ibrutinib, and 1 with 5 prior lines of rituximab-based therapy. See, FIGS. 2 and 4.

Of the four mantle cell lymphoma (MCL) patients, 100% of patients (4 of 4) achieved an objective response with 2 patients achieving a complete response (CR), as determined by radiography with bone marrow confirmation pending, and 2 patients achieving a partial response (PR). See, FIGS. 2 and 4. One MCL patient remains on study now for close to 800 days. (FIG. 3).

The 5 patients who showed progressive disease (PD) on study had Diffuse Large B-Cell Lymphoma (DLBCL). The DLBCL patients had a median of four prior therapies, and 4 out of the 6 patients with DLBCL were of the non-germinal center B-cell-like (GCB) subtype. See, FIG. 4.

Duration of Study:

81% of patients were on the study for more than 6 months. The median time on the study was 11.1 months (range 0.4-30.1+ months). (See FIG. 3). One CLL patient and one FL patient has been on the study for over 900 days. FIG. 3.

CONCLUSIONS

This is the first triple combination of an anti-CD20 antibody, a P13K-delta inhibitor, and a BTK inhibitor used to treat B-cell malignancies. The combination of UTX+ TGR-1202+ibrutinib was well-tolerated with clinical activity observed across heavily pre-treated and high-risk B-cell malignancies.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

---

What is claimed is:

1. A method of treating chronic lymphocytic leukemia (CLL), marginal zone lymphoma (MZL), small lymphocytic lymphoma (SLL) or mantle cell lymphoma (MCL) in a subject which comprises
(a) administering to the subject a combination of agents, for a time and in therapeutically effective amounts to treat said CLL, MZL, SLL or MCL, said combination of agents comprising:
(i) at least one PI3K-delta selective inhibitor represented by Formula A, a stereoisomer thereof, a pharmaceutically acceptable salt, or solvate, thereof:

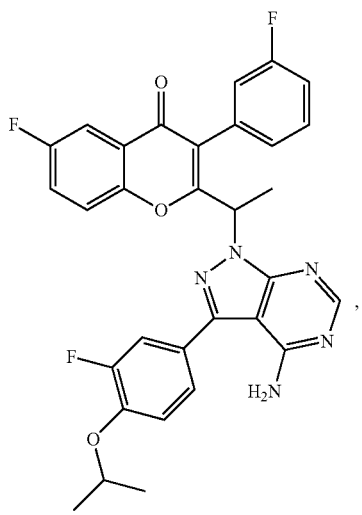

(A)

selected from
(RS)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; or
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(ii) at least one anti-CD20 antibody or an antigen-binding fragment thereof,
wherein said anti-CD20 antibody is ublituximab or an anti-CD20 antibody that binds to the same epitope as ublituximab; and
(iii) at least one inhibitor of Bruton's tyrosine kinase (BTK) wherein said, wherein the BTK inhibitor is ibrutinib; and
(b) reducing said subject's baseline disease burden by at least 50% by the first efficacy assessment.

2. The method of claim 1, wherein the PI3K-delta inhibitor is administered at a dosage from: about 200 mg to about 1200 mg, about 400 mg to about 1000 mg, about 400 mg to about 800 mg, about 400 mg, about 500 mg, about 600 mg, about 700 mg, about 800 mg, about 900 mg, about 1000 mg, or about 1200 mg.

3. The method of claim 1, wherein the PI3K-delta inhibitor is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one or a pharmaceutically acceptable salt thereof.

4. The method of claim 3, wherein the PI3K-delta inhibitor is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one p-toluenesulfonic acid salt (TGR-1202).

5. The method of claim 4, wherein TGR-1202 is administered at a dose from (a) about 400 mg to about 1200 mg per day or (b) about 800 mg per day.

6. The method of claim 1 or 3, wherein said anti-CD20 antibody is ublituximab.

7. The method of claim 6, wherein said ublituximab comprises (i) the VH CDR1, CDR2, and CDR3 region of sequences SEQ ID NOS: 1, 2, and 3, and the VL CDR1, CDR2, and CDR3 region of sequences SEQ ID NOS: 6, 7, and 8, or (ii) the VH of SEQ ID NO: 4 and the VL of SEQ ID NO: 9.

8. The method of claim 6, wherein ublituximab is administered at a dose from: about 450 mg to about 1200 mg, about 600 to about 1200 mg, about 600 to about 1000 mg, about 600 to about 900 mg, about 600 mg, about 700 mg, about 800 mg, or about 900 mg about once every 1 to 9 weeks, about once every week, about twice every week, about once every 2 weeks, about once every 3 weeks, about once every 4 weeks, about once every 5 weeks, about once every 6 weeks, about once every 7 weeks, about once every 8 week, or about once every 9 weeks.

9. The method of claim 8, wherein ublituximab is administered at a dose of about 900 mg.

10. The method of claim 1, wherein the BTK inhibitor is ibrutinib administered once daily at a dosage from: about 400 to about 600 mg, about 400 mg, about 420 mg, about 440 mg, about 480 mg, about 500 mg, about 520 mg, about 540 mg, about 560 mg, about 580 mg, or about 600 mg.

11. The method of claim 10, wherein ibrutinib is administered once daily at a dosage of about 420 mg or about 560 mg per day.

12. The method of claim 1, wherein said CLL, MZL, SLL or MCL overexpresses CD20, is refractory to chemotherapy or has relapsed.

13. The method of claim 12, wherein the CLL, MZL, SLL or MCL is refractory to an anti-CD20 antibody, a PI3K-delta inhibitor, or a BTK inhibitor.

14. The method of claim 1, wherein said combination of agents i, ii, and iii are administered separately and/or sequentially.

15. The method of claim 1, wherein said agents i and iii are administered simultaneously or sequentially once a day, and, optionally, are contained in the same pharmaceutical composition.

16. A method of treating chronic lymphocytic leukemia (CLL), marginal zone lymphoma (MZL), small lymphocytic lymphoma (SLL) or mantle cell lymphoma (MCL) in a human subject which comprises,
   (a) administering to said subject a combination of agents, in therapeutically effective amounts to treat said CLL, MZL, SLL or MCL, said combination of agents comprising:
      (i) TGR-1202;
      (ii) ublituximab; and
      (iii) a Bruton's tyrosine kinase (BTK) inhibitor, wherein the BTK inhibitor is ibrutinib; and
   (b) reducing said subject's baseline disease burden by at least 50% by the first efficacy assessment.

17. The method of claim 1, wherein step (b) reduces disease burden by at least 75%.

18. The method of claim 16, wherein step (b) reduces disease burden by at least 75%.

19. A method of depleting a B-cell population in a subject with excessive B-cell proliferation, which comprises
   (a) administering to said subject a combination of agents, for a time and in therapeutically effective amounts to treat a disease or disorder associated with excessive B-cell proliferation, said combination of agents comprising:
      (i) at least one PI3K-delta selective inhibitor, wherein said PI3K-delta selective inhibitor is a compound of Formula A, a stereoisomer thereof, a pharmaceutically acceptable salt, or solvate, thereof:

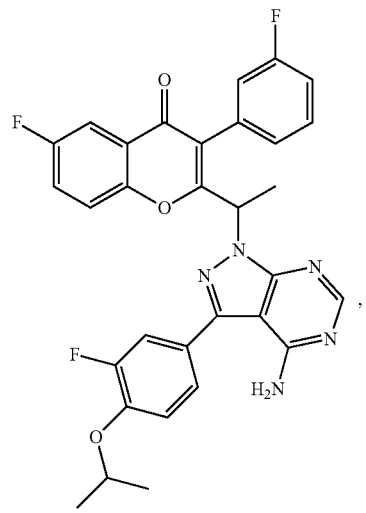

(A)

selected from (RS)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; or (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
      (ii) at least one anti-CD20 antibody or an antigen-binding fragment thereof, wherein said anti-CD20 antibody is ublituximab or an anti-CD20 antibody that binds to the same epitope as ublituximab; and
      (iii) at least one Bruton's tyrosine kinase (BTK) inhibitor, wherein the BTK inhibitor is ibrutinib; and
   (b) depleting said B-cells in said B-cell population.

20. The method of claim 5, wherein TGR-1202 is administered at a dose of about 800 mg per day.

* * * * *

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Ublituximab Variable heavy chain CDR1

<400> SEQUENCE: 1

Gly Tyr Thr Phe Thr Ser Tyr Asn
1               5

<210> SEQ ID NO 2
<211> LENGTH: 8
<212> TYPE: PRT
<213> ORGANISM: Artificial Sequence
<220> FEATURE:
<223> OTHER INFORMATION: Ublituximab Variable heavy chain CDR2

<400> SEQUENCE: 2

Ile Tyr Pro Gly Asn Gly Asp Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Ublituximab Variable heavy chain CDR3

<400> SEQUENCE: 3

Ala Arg Tyr Asp Tyr Asn Tyr Ala Met Asp Tyr
1               5                   10

<210> SEQ ID NO 4
<211> LENGTH: 118
<212> TYPE: PRT
<213> ORGANISM: Artificial Sequence
<220> FEATURE:
<223> OTHER INFORMATION: Ublituximab Variable heavy chain

<400> SEQUENCE: 4

Gln Ala Tyr Leu Gln Gln Ser Gly Ala Glu Leu Val Arg Pro Gly Ala
1               5                   10                  15
```

```
Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Gly Ile Tyr Pro Gly Asn Gly Asp Thr Ser Tyr Asn Gln Lys Phe
    50                  55                  60

Lys Gly Lys Ala Thr Leu Thr Val Gly Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Asp Tyr Asn Tyr Ala Met Asp Tyr Trp Gly Gln Gly Thr
                100                 105                 110

Ser Val Thr Val Ser Ser
            115

<210> SEQ ID NO 5
<211> LENGTH: 330
<212> TYPE: PRT
<213> ORGANISM: Artificial Sequence
<220> FEATURE:
<223> OTHER INFORMATION: Ublituximab Constant heavy chain

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 5
<212> TYPE: PRT
<213> ORGANISM: Artificial Sequence
<220> FEATURE:
<223> OTHER INFORMATION: Ublituximab Variable light chain CDR1

<400> SEQUENCE: 6

Ser Ser Val Ser Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: Ublituximab Variable light chain CDR2

<400> SEQUENCE: 7

Ala Thr Ser
1

<210> SEQ ID NO 8
<211> LENGTH: 9
<212> TYPE: PRT
<213> ORGANISM: Artificial Sequence
<220> FEATURE:
<223> OTHER INFORMATION: Ublituximab Variable light chain CDR3

<400> SEQUENCE: 8

Gln Gln Trp Thr Phe Asn Pro Pro Thr
1               5

<210> SEQ ID NO 9
<211> LENGTH: 106
```

```
<212> TYPE: PRT
<213> ORGANISM: Artificial Sequence
<220> FEATURE:
<223> OTHER INFORMATION: Ublituximab Variable light chain

<400> SEQUENCE: 9

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Phe Thr Ile Ser Arg Val Glu Ala Glu
65                  70                  75                  80

Asp Ala Ala Thr Tyr Tyr Cys Gln Gln Trp Thr Phe Asn Pro Pro Thr
                85                  90                  95

Phe Gly Gly Gly Thr Arg Leu Glu Ile Lys
            100                 105

<210> SEQ ID NO 10
<211> LENGTH: 106
<212> TYPE: PRT
<213> ORGANISM: Artificial Sequence
<220> FEATURE:
<223> OTHER INFORMATION: Ublituximab Constant light chain

<400> SEQUENCE: 10

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```